US012343237B2

(12) United States Patent
Bogdanic et al.

(10) Patent No.: US 12,343,237 B2
(45) Date of Patent: Jul. 1, 2025

(54) METHOD FOR GRAPHICALLY PRESENTING A PLURALITY OF SCANS

(71) Applicant: 3SHAPE A/S, Copenhagen K (DK)

(72) Inventors: Alen Bogdanic, Brøndby Strand (DK); Admir Huseini, Copenhagen K (DK); Daniella Alalouf, Copenhagen K (DK)

(73) Assignee: 3SHAPE A/S, Kobenhavn K (DK)

( * ) Notice: Subject to any disclaimer, the term of this patent is extended or adjusted under 35 U.S.C. 154(b) by 925 days.

(21) Appl. No.: 17/437,892

(22) PCT Filed: Mar. 11, 2020

(86) PCT No.: PCT/EP2020/056573
§ 371 (c)(1),
(2) Date: Sep. 10, 2021

(87) PCT Pub. No.: WO2020/182920
PCT Pub. Date: Sep. 17, 2020

(65) Prior Publication Data
US 2022/0168074 A1    Jun. 2, 2022

(30) Foreign Application Priority Data

Mar. 11, 2019 (EP) .................................... 19161975

(51) Int. Cl.
*A61C 9/00* (2006.01)
*G06T 7/00* (2017.01)
*G16H 30/40* (2018.01)

(52) U.S. Cl.
CPC .......... *A61C 9/0053* (2013.01); *G06T 7/0012* (2013.01); *G16H 30/40* (2018.01); *G06T 2207/30036* (2013.01)

(58) Field of Classification Search
CPC ................ A61C 9/0053; G06T 7/0012; G06T 2207/30036; G16H 30/40
See application file for complete search history.

(56) References Cited

U.S. PATENT DOCUMENTS

| 7,077,647 B2 | 7/2006 | Choi et al. |
| 7,160,110 B2 | 1/2007 | Imgrund et al. |
| 9,510,757 B2 | 12/2016 | Kopelman et al. |

(Continued)

FOREIGN PATENT DOCUMENTS

| EP | 3050534 B1 | 4/2018 |
| WO | 2017144647 A1 | 8/2017 |

OTHER PUBLICATIONS

International Search Report (PCT/ISA/210) and Written Opinion (PCT/ISA/237) mailed on Apr. 23, 2020, by the European Patent Office as the International Searching Authority for International Application No. PCT/EP2020/056573.

(Continued)

*Primary Examiner* — Ping Y Hsieh
*Assistant Examiner* — Jose M Torres
(74) *Attorney, Agent, or Firm* — Buchanan Ingersoll & Rooney PC

(57) ABSTRACT

Disclosed is a system and method for presenting a graphical representation of an oral situation of a patient over time. In particular the system and method relates to a method of presenting a plurality of scans taken over time in manner where the focus on the changes in the oral situation of the patient is maintained.

16 Claims, 28 Drawing Sheets

(56) References Cited

U.S. PATENT DOCUMENTS

| | | | |
|---|---|---|---|
| 9,626,462 B2 | 4/2017 | Somasundaram et al. | |
| 2004/0029068 A1* | 2/2004 | Sachdeva | G16H 50/50 |
| | | | 433/24 |
| 2008/0057478 A1* | 3/2008 | Choi | A61C 9/004 |
| | | | 433/215 |
| 2010/0208967 A1 | 8/2010 | Wilson et al. | |
| 2013/0308843 A1* | 11/2013 | Tank | G06T 7/12 |
| | | | 382/128 |
| 2016/0125651 A1* | 5/2016 | Lior | G06T 19/20 |
| | | | 382/154 |
| 2016/0302895 A1* | 10/2016 | Rohaly | A61C 9/0053 |
| 2017/0236327 A1* | 8/2017 | Somasundaram | G06T 19/20 |
| | | | 345/419 |
| 2018/0005371 A1* | 1/2018 | Sabina | A61C 9/0046 |
| 2018/0235437 A1* | 8/2018 | Ozerov | A61B 5/4552 |
| 2019/0008446 A1* | 1/2019 | Cunliffe | A61B 5/1078 |
| 2020/0107915 A1* | 4/2020 | Roschin | A61C 13/34 |

OTHER PUBLICATIONS

Grauer, D., et al., "Accuracy in tooth positioning with a fully customized lingual orthodontic appliance", American Journal of Orthodontics and Dentofacial Orthopedics, Sep. 2011, vol. 140, No. 3, pp. 433-443.

Jacobs, C., et al., "Single tooth torque correction in the lower frontal area by a completely customized lingual appliance", Head & Face Medicine, Oct. 10, 2017, vol. 13, No. 1, 6 pages.

M. Málková, "Morphing of Geometrical Objects in Boundary Representation" The State of the Art and the Concept of PhD. Thesis, University of West Bohemia in Pilsen, Apr. 2010. (63 pages).

B. Mocanu, "3D Mesh Morphing" Economics and Finance, Institut National des Telecommunications, HAL, Nov. 29, 2012. (186 pages).

J. Parus, "Morphing of Meshes" The State of the Art and Concept of PhD. Thesis, University of West Bohemia in Pilsen, CZ, Apr. 2005. (74 pages).

* cited by examiner

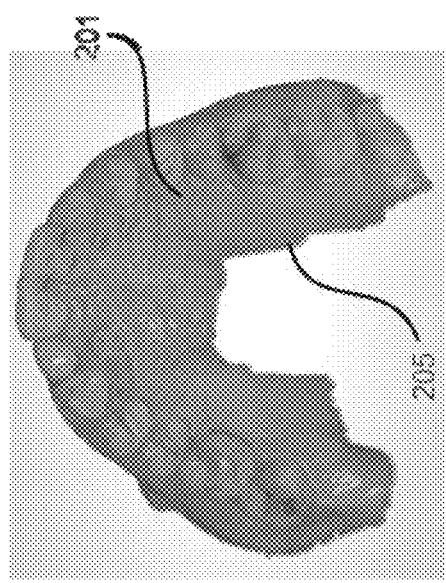
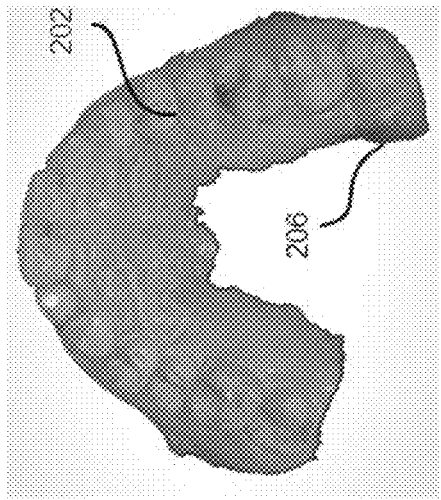
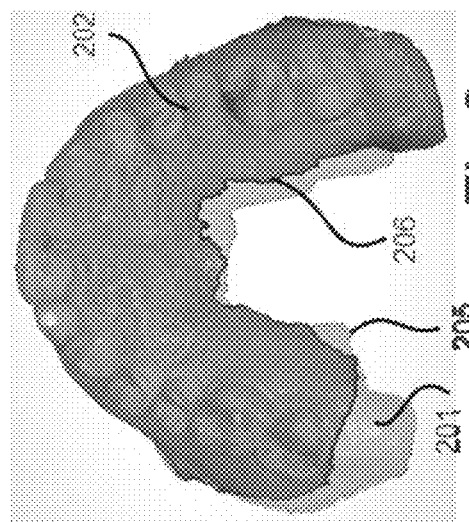
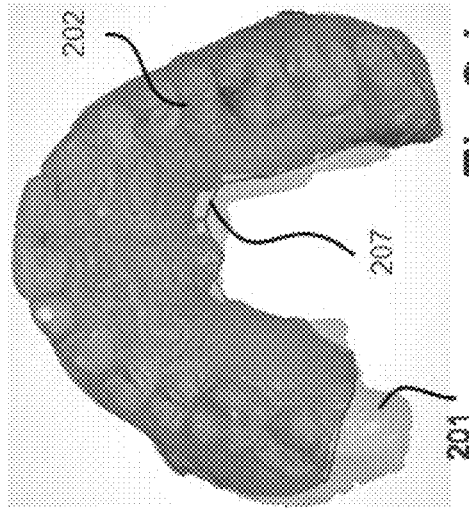

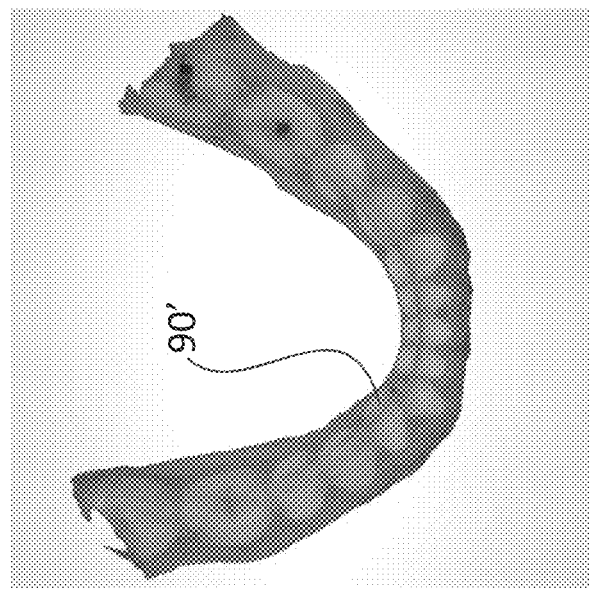
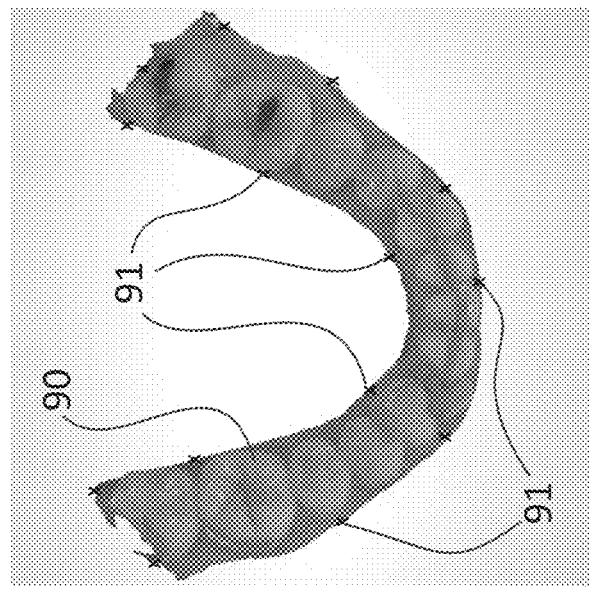
Fig.10a
Fig.10b

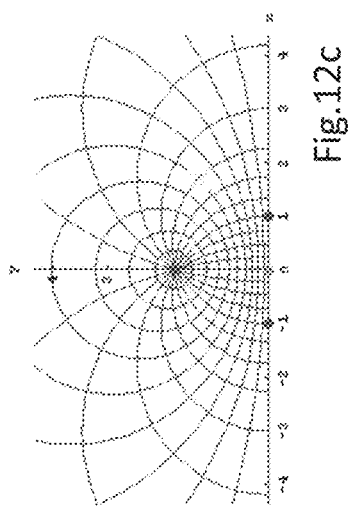
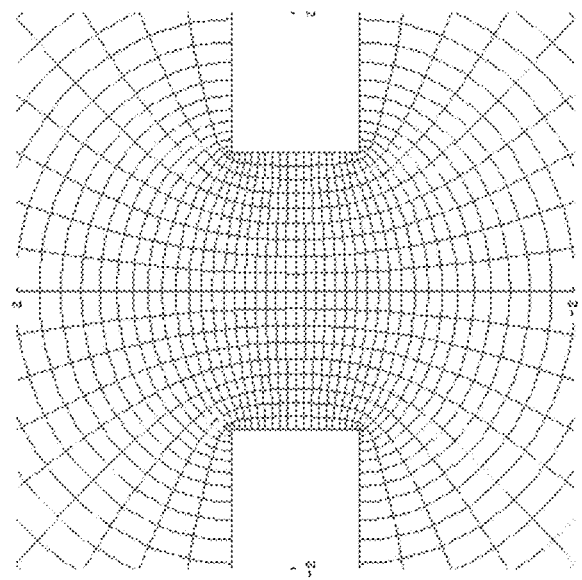
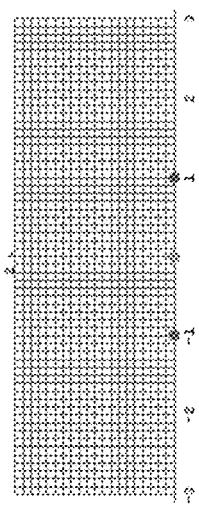
Fig.12c
Fig.12b
Fig.12a

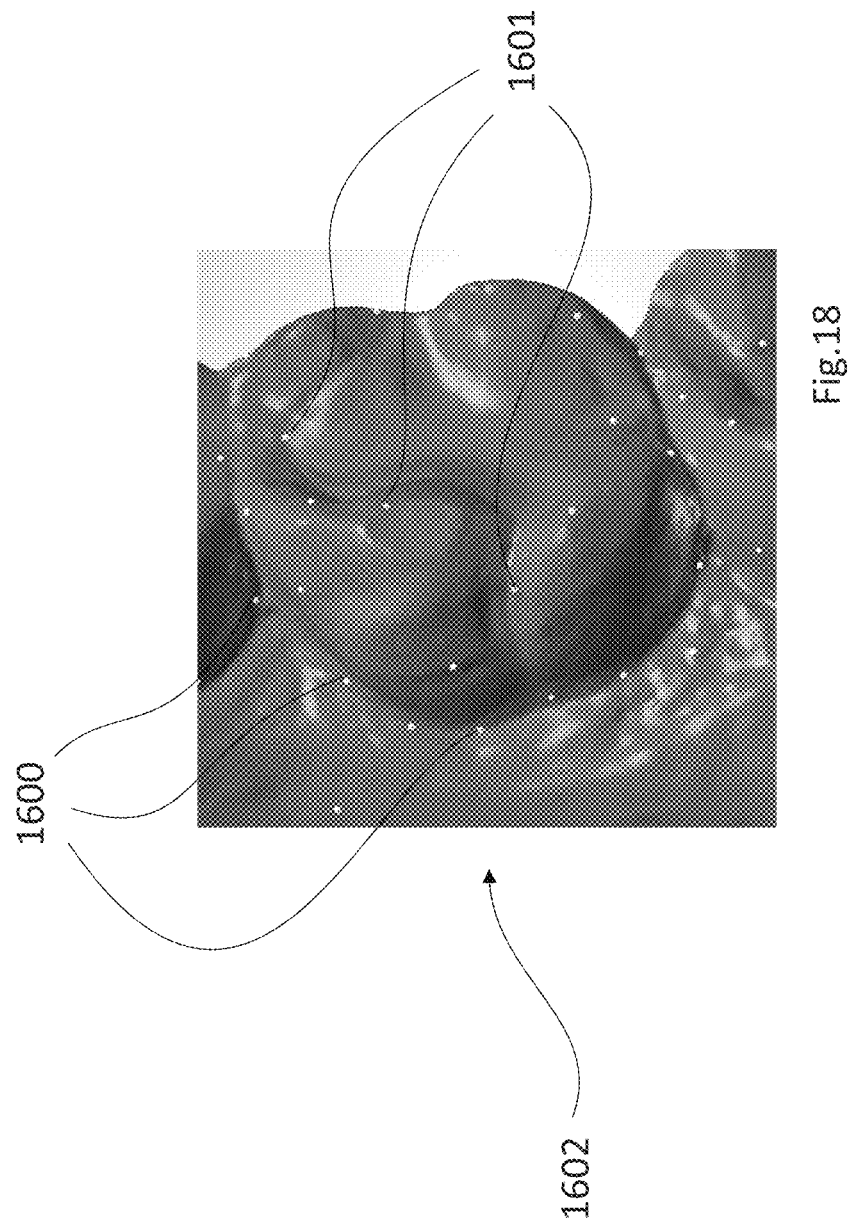

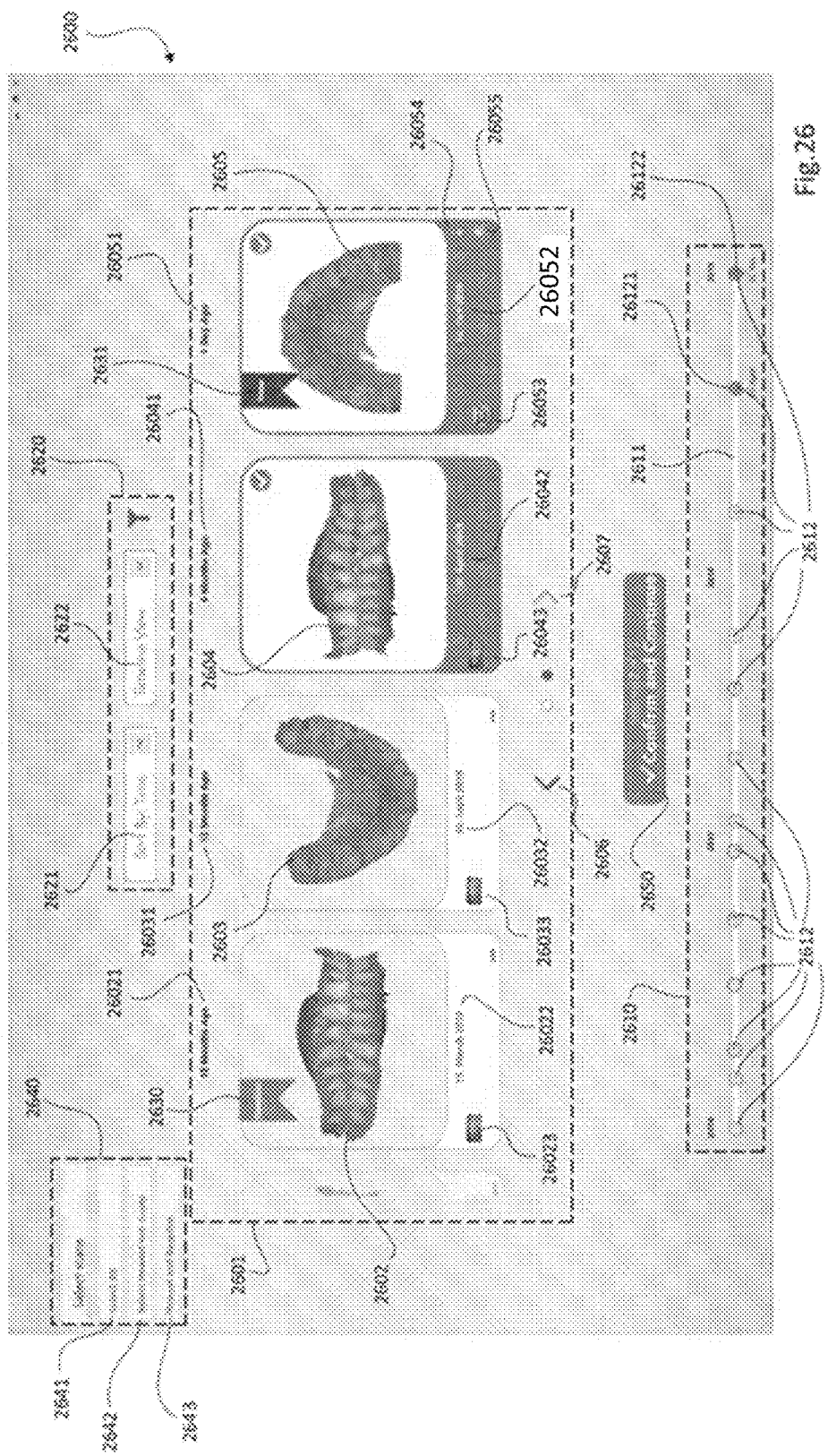

METHOD FOR GRAPHICALLY PRESENTING A PLURALITY OF SCANS

FIELD OF THE INVENTION

This invention generally relates to a system and method for presenting a graphical representation of an oral situation of a patient over time and a user interface for selecting a plurality of scans for use in such a method. In particular the system and method relates to a computer implemented method of presenting a plurality of scans taken over time in manner where the focus on the changes in the oral situation of the patient is maintained.

BACKGROUND OF THE INVENTION

The current disclosure relates to comparing scans of a patient's oral situation, e.g. teeth, gingiva and soft tissue taken over time.

In particular with the introduction and acceptance of so-called intra oral scanning a new way of monitoring a patients oral health has evolved. This is particularly due to the fact that data from different scanning sessions can be compared and analysed, which provides the doctor with a detailed tool for determining even small changes over time and there by initiate preventive actions.

However, when it comes to presenting such changes visually, for example graphically on a monitor, it is important that the information relayed relates to the clinical changes of the patient while other changes occurring from for example the extent of soft tissue as a consequence of how the teeth were scanned during the different patient visits are reduced or removed.

SUMMARY OF THE INVENTION

In one aspect there is disclosed a computer implemented method for presenting a graphical representation of an oral situation of a patient over time, wherein the method comprises,
  obtaining a plurality of scans, each scan representing the oral situation of the patient at a specific time, and where each scan comprises a scan boundary defining the extent of the scan,
  determining at least one modified boundary, and
  presenting the plurality of scans in a time sequence wherein the scan boundary of each of the respective plurality of scans has been modified based on one of the at least one modified boundary.

By providing a modified boundary as described herein it is possible to provide a graphical presentation of the change in the patients oral situation over time where uneven scan edges and redundant scan data can be modified and thereby an even graphical presentation can be provided.

This has the advantage that the focus from the health care professional will be maintained on clinical changes in the scans that are relevant for an evaluation of the historical changes of a patient.

Presenting the plurality of scans in a time sequence is typically done on a computer monitor, for example a screen, smart phone or digital glasses.

The scans can be shown in a sequence next to each other. A scrolling function can for example be used so that the user can scroll through the plurality of scans, e.g. on the computer monitor.

Two scans could be selected from the plurality of scans and a slider function on the user interface allows for fast swap back and forth between the selected scans of interest.

In a preferred embodiment the plurality of scans are presented by aligning the scans in a common coordinate system and then present them graphically in a time sequence determined by when the scans were acquired where the computer will display a transition between the scans. This provides an animation where the viewer will be able to see visually discernible changes between the scans. The transition may further comprise morphing between the scans.

Aligning the scans can for example be done manually, by identifying at least three common points on the respective scan and/or using an ICP (Iterative Closest Point) algorithm. These methods of aligning are commonly known in the art and are often used to arrange similar 3D models in a common coordinate system in order to align them together.

The plurality of scans may represent the full oral situation, i.e. both the upper and lower jaw where both arches has been fully scanned. However, it is also possible to use a plurality of partial scans and graphical present these in a time sequence as discussed herein.

The advantage of the current method is as discussed; that a plurality of scans can be visually presented and compared, in particular in order to visually inspect how the oral situation of the patient may have changed over time. This requires a plurality of scans obtained through a number of scanning sessions. In this context the plurality of scans does not necessarily have to include all the scans taken over time but may comprise a subset of scans chosen as suitable for use in the method as disclosed. The plurality of scans can thus for example be selected from a larger collection of scans but may have been chosen due to quality of scans, the scans where taken at desired time intervals or of many other reasons.

One example of presenting a smooth transition between scans which is modified according to different modified boundaries is done by morphing.

This concept will allow for a smooth transition between small variations when displayed in a time sequence.

In particular where the plurality of scans are in the form of surface data, e.g. using meshes which is well known in the art, morphing can in one embodiment be done based on mesh parametrization:

The key point is to map both models to a common simple surface like plane or sphere as a common reference, also referred to generally as a base domain herein.

In general mesh morphing is a well studied and well understood problem in the field of 3d graphics. Given two meshes A and B, there are many standard approaches to generate a new predetermined mesh C whose vertex positions vary according to a coefficient t in the interval [0,1] so that C0=A, C1=B and the meshes Ct represent an intermediate state of the vertex positions interpolated between A and B. The morphing visualization is realized by creating an animation consisting of n frames and showing the mesh C with interpolation value $t=i/n$, where "i" is an integer that varies between 0 and n.

However, in one embodiment the step presenting the plurality of scans in a time sequence wherein the scan boundary of each of the respective plurality of scans has been modified based on one of the at least one modified boundary, comprises that the modified boundary is used as a reference for morphing between at least two of the plurality of scans in a time sequence.

By using the modified boundary as a reference for morphing a solution is provided which is particularly suited for morphing between different scans of a dental situation as disclosed herein.

Sophisticated morphing can furthermore be applied which is particular advantageous when looking at a jaw over time where changes to teeth and gingiva but also other components such as bracket placement occur over time.

Accordingly there is disclosed a morphing algorithm that comprises a parametrization process, a feature alignment process, a remeshing process, and a rendering process.

In one embodiment a base domain is defined based on the at least one modified boundary. This can for example be done by fitting a plane through the at least one modified boundary, projecting the at least one modified boundary to the plane and defining the base domain as the plane defined by the projected at least one modified boundary.

Additionally, the scan boundary of the plurality of scans can be set as the at least one modified boundary. This can thus be used as a reference to align the respective scans to the base domain.

In one embodiment each of the plurality of scans are mapped to the base domain and each of the plurality of scans may further be flattened to the base domain.

In order to flatten a scan different constraints may be used. For example specific points on the scans are constrained to be mapped to specific point in the base domain. Furthermore, in one embodiment meshes where the teeth are segmented the teeth can be used as a further reference in order to ensure proper flattening by using one, more or all of the teeth as anchor points or anchor areas/volumes.

Typically the actual flattening is done by a Laplacian algorithm, which is a process that is well known in the art.

With the plurality of scans arranged in the base domain, or alternatively treating each of the plurality of scans one at the time, a predetermined mesh may advantageously be applied to each of the plurality of scans when mapped to the base domain. This provides a common structure for the plurality of scans where one vertex in one scan have a one-to-one correspondence with a respective vertex in each of the other plurality of scans.

The plurality of scans may then be returned to the 3D domain. In one embodiment this is done by returning the vertices of the predetermined mesh into the 3D domain.

Accordingly using the predetermined mesh data in one embodiment morphing between the plurality of scans in a time sequence can be provided by linearly transforming between corresponding vertices in the predetermined mesh of the respective plurality of scans.

In yet a further embodiment a morphing algorithm/method is also applied to the color of the plurality of scans. This is particularly advantageous where the color of the plurality of the scans are different between scans. Such difference in colors may for example be due to using different scanner or differently calibrated scanner for some or all of the scans. It may also be the result of differences in the ambient lighting when some or all of the scans were taken. Morphing therefore allow for a graphical presentation of the plurality of scans in a time sequence where changes in the color are smooth and visually pleasing.

In one embodiment the step presenting the plurality of scans in a time sequence wherein the scan boundary of each of the respective plurality of scans has been modified based on one of the at least one modified boundary, comprises that the scan boundary of each of the respective plurality of scans is at least partly modified to one of the at least one modified boundary.

This provides an even graphical presentation over time as discussed since the respective scan boundaries are modified to visualise a more uniform shape of the plurality of scans.

As discussed herein the scans are modified in order to enable a uniform graphical presentation of the oral situation over time and in particular it is the scan boundaries that may be uneven and comprise data that may be graphically and visually interrupting during presentation and which does not represent an actual clinical situation of the patient oral situation.

Accordingly, at least one modified boundary is determined and the plurality of the scans are modified based on the one or more modified boundaries which has been determined.

One such modified boundary can be a pre-set boundary, e.g. a template boundary. The pre-set boundary can then be used as a cookie-cutter for one or more of the plurality of scans and thereby ensure a uniform scan boundary. In the current specification a pre-set boundary should be understood as a modified boundary which is not customised based on data derived from the plurality of scans. However, the pre-set boundary may be selected based on data of the patient as described below.

The method may encompass several pre-set boundaries. Thus, a first pre-set boundary may be used for scans that were taken during childhood, a second pre-set boundary may be used for scans that were taken during adolescence and a third pre-set boundary may be used for scans taken during adulthood. In other embodiment the pre-set boundary may also be determined based the patients sex.

In a related example, the pre-set boundary is based on a preferred manual trimming outline performed by the healthcare professional subsequent to and or while acquiring a scan according to personal preferences. This manually trimmed outline could be stored as a preferred outline for that specific patient and can be applied as a default trimming outline in following cases.

In general, using a pre-set boundary has the advantage of avoiding processing one or more of the plurality of scans in order to determine a modified boundary. This can in particular be an advantage in setups with low computer processing power.

In another embodiment the at least one modified boundary is determined based on a reference scan selected from the plurality of scans.

In one embodiment thereof the scan boundary of the reference scan is set as the at least one modified boundary. This can be a simple way of determining a modified boundary since the boundary of one scan can simply be copied onto other scans and can thus for example be implemented on a computer system with a low processing power.

However, in an alternative embodiment the reference scan can be further processed in order to determine a modified boundary. For example, by smoothing the boundary of the reference scan or performing hole filling before applying it as the boundary on the rest of the plurality of scans.

In another embodiment the at least one modified boundary is determined based on at least two of the plurality of scans. This has the advantage that data from the at least two scans can be used to determine the modified boundary and thereby provide a better estimate on a modified boundary that fits a number of the plurality of scans. This can for example be advantageous in that the scans requires less post-processing since actions such as trimming and filling will be less cumbersome. It is also an advantage that this provides an improved visual experience when the graphical representation of the oral situation over time is presented.

In one exemplary embodiment when determining the at least one modified boundary based on at least two of the plurality of scans the method may further comprise, determining at least a first and a second scan boundary of the at least two of the plurality of scans respectively, and determining the at least one modified boundary based on an average boundary of the at least first and second scan boundary.

In one embodiment the at least one modified boundary is further processed, for example the of determining the at least one modified boundary may further comprise the step of smoothing the average boundary. Or, alternatively or additionally, each of the at least first and second boundary are smoothed before determining the at least one modified boundary.

The plurality scans may span a large time period, such as scans taken from childhood and through adulthood and ageing covering many natural physical changes. They may also cover a period where substantial physical jaw changes have occurred, such as surgery or other dental treatments. In such cases a plurality of modified boundaries can advantageously be determined comprising at least a first and a second modified boundary. These plurality of modified boundaries can then better fit the respective scans.

For example, the first common and second modified boundary are pre-set boundaries with a different size and/or shape.

Or, alternatively in another embodiment the first modified boundary is determined based on at least two of the plurality of scans and wherein the second modified boundary is determined based on at least two of the plurality of scans, where at least one of the two of the plurality of scans for determining the second modified boundary is different from the at least two of the plurality of scans for determining the first modified boundary.

The plurality of modified boundaries may in some embodiments have been provided using different methods. For example, the first modified boundary can a pre-set boundary and the second modified boundary can be determined based on at least two of the plurality of scans.

In one embodiment the scan boundaries of the scans of a first group of the plurality of scans is modified to the first modified boundary, and the scan boundaries of the scans of a second group comprising scans different from the first group of the plurality of scans is modified to the second modified boundary.

And even further the plurality of modified boundaries may in a further embodiment comprises a third or more modified boundaries comprising either a pre-set boundary or a boundary determined based on at least two of the plurality of scans.

Accordingly, when grouping is provided as disclosed a third or more group can further be provided comprising a number of the plurality of scans different from the scans of the other groups, where the scan boundaries of the scans of the third group or more group are modified to the third or more modified scan boundaries respectively.

Such grouping can advantageously be provided in embodiments where the first, second, third and/or more groups are determined based on one or more time variable of the scans in the respective groups.

Advantageously such time variable can be the age of the patient when the specific scan was taken.

Or, alternatively or additionally, the time variable can be a patient size parameter taken when the specific scan was taken, such as height and/or weight.

In an even further embodiment, the time variable can be the time from when a dental treatment was initiated or completed.

Additionally, or alternatively, the first, second, third and/or more groups can also be determined based on one or more patient characteristic, such as sex.

Accordingly, it is possible to change the scan boundary if so needed in order to accommodate for substantive changes in the scan but still maintain a graphical presentation which focus on the actual changes of the patient.

In one embodiment the scan boundary of at least two scans are modified to have the same at least one modified boundary. This has the advantage that no change is observable in the scan boundary of the scans as they are presented in a graphical representation over time.

A simple embodiment may be provided wherein the at least one modified boundary is set to be the scan boundary of one of the plurality of scans and wherein the scan boundary of at least a second of the plurality of scans is modified to the at least one modified boundary. This requires low processing resources when determining the modified boundary.

In order to process the scans and the at least modified boundary in a digital environment, the at least modified boundary can advantageously be represented as a digital design tool. For example, in one such embodiment the at least one modified boundary is a closed spline. A spline is often used in CAD (Computer-Aided-Design) software as a tool representing a line, either straight or curved. It does not have to be closed, it can for example also be open.

The spline can for example be used as a cutting spline for removing or masking scan data outside the cutting spline. The spline may additionally be fused into the scan data in order to make a smooth boundary.

Or the spline can additionally or alternatively be used as a fill spline for adding data to the scan data within the fill spline.

Adding data could for example be done by importing patches of the missing surface structure from the template scan and fusing it into the model suffering from insufficient data in some regions.

Adding data could for example also be done by hole closing, where numerous hole closing algorithms are known in the art.

In one embodiment, where the scan is a surface scan and digitally generated as a triangle mesh the hole closing may be performed by using the following steps:

1. In context of this application, the hole geometry/area that needs to be filled is specified by the spline and the model boundary. A hole closing requirement that the hole boundary is a single-component curve can be satisfied by introducing an edge connecting the pair of closest points between the spline and boundary of the model.
2. Hole closing and clean-up. Hole closing is iterated up to 10 times, or until there are no more holes left. It is performed by ear clipping algorithm, which creates a heap structure for all candidate triangles. The heap is partially order by determining scores for each candidate triangle.

At every iteration the triangle with the highest positive score is removed from the heap and introduced into the hole closing patch. Then the heap is updated to include new candidates. The score function is designed in a way that promotes smooth hole closing patch, without self-intersections or otherwise invalid configurations. In context of this application, this would require enforcing continuity of the surface normal vector across the model's boundary and possibly a penalty term on the length of introduced edges.

At the end of each iteration of hole closing, a clean-up is performed where vertices are removed together with neighboring triangles if they are in pick-up (non-manifold) configuration, or if their normal vectors are not consistent with (pointing away from) the normals of neighboring facets.

3. Hole closing patch improvement through refinement, smoothing and decimation.
4. Patch coloring: The colors are propagated to the new vertices from the nearest neighbors on the model, for which the colors are already defined (nearest neighbor interpolation).

Numerous ways of providing digital data and represent then visually are provided in the art. For example, the plurality of scans can be obtained as voxel data.

In other embodiment the plurality of scans can be obtained as surface data.

In such embodiment, the surface data can be further processed so that the plurality of scans are obtained as volumetric data.

Besides the processing described herein at least one of the plurality of scans may be further processed between obtaining the scans and presenting the plurality of scans.

For example, the plurality of scans can be segmented to digitally identify teeth of the scans and gingiva of the scans. This may further aid the system to determine at least one modified boundary as disclosed herein.

In aspect disclosed herein is a user interface for facilitating the selection of the plurality of scans from a database or library of patient scans taken over time.

Since it is becoming even more usual to take an intra oral scan when a patient visits a patient digital record is expanding rapidly with 3D scans taken at different points in time. Thus the user will have to select the relevant scans for processing for providing a graphical presentation of the oral situation over time.

For example, considering different cases where the user might want to see how the patients dental situation has evolved over time it can be understood the same scans are not necessarily useful. For example in a general overview showing the patient oral dentition over the last twenty years a plurality of scans spaced appropriately apart in time will be a good starting point. However, using a mid-treatment scan, e.g. a scan with a preparation or a visible implant will generate a unfortunate presentation. However, if a user desired to monitor a patients treatment, e.g. orthodontic treatment, it is relevant to use scans obtained over different points in time during that treatment process.

The ability to select of subset of scans and forward only that particular subset into the next software module, which is handling the scan analysis functionality such as simulations of movement between scans and scan to scan comparison, provides a much more targeted analysis environment. Only relevant information are processed and displayed in the analysis software module. This provides a faster processing time and a mores clean presentation platform, where only the case specific information are displayed. This enables the health care professional to do focused analysis and the ability to share, educate and discuss only the case relevant information together with the patient. One example could be, that the health care professional want to inform a patient amount progress in tooth ware due to grinding. The healthcare professional select only the subset of scans related to the progress in tooth ware and are able to show the information to the patient. This function provides support for the clinical evaluation and the final treatment which the health care professional and the patient may agree to perform.

Accordingly, a user interface for selecting a plurality of scans for use in graphically presenting the scans over time is provided, wherein the user interface comprises a first area wherein an image of at least two of the plurality of scans is shown and a second area showing a time line whereon the time for taking the at least two of the plurality of scans is shown and wherein the time line at least show one additional scan from the plurality of scans which is not shown in the first area.

In another aspect the data generated in the method for presenting a graphical representation of an oral situation of a patient over time as disclosed herein may also be used to train a neural network.

Even further the input from the user in the user interface to select the plurality of scans may also be used to train a neural network in order to provide a system that may automatically generate a graphical representation over time based on the scan data available in the scan resource.

As discussed herein it is understood that the method disclosed is advantageous for presenting scans of a patient that was taken at different times and provides an improved graphical representation of the changes.

The method is thus preferable a digital computer implemented method where the presenting the graphical representation is done on a monitor or similar output device which is capable of visually displaying a graphical model. For example, a smart phone, tablet or a computer monitor.

The step of obtaining a plurality of scans me be done by loading or accessing them from a database, either locally or in the cloud. The scans can initially been obtained by intra orally scanning the patient or they may have been provided through physical impressions of the teeth, which subsequently have been digitalised.

The step of determining the at least one modified boundary can also be done in different ways in a digitally design environment.

As disclosed a template or pre-set boundary is selected from a menu and used as a cookie cutter. The computer implemented method may also comprise a semi- or fully automated algorithm which determines the at least modified boundary by analysing one or more of the plurality of scans as described above in respect to the disclosed method.

Finally, presenting the plurality of scans in a time sequence ties the computer implement method together since this, as disclosed above, is typically done as a graphical representation on e.g. a monitor or other displaying device.

In further aspects the method disclosed herein is computer implemented and may be provided on a computer, in a computer network or other programmable apparatus.

BRIEF DESCRIPTION OF THE DRAWINGS

The above and/or additional objects, features and advantages of the present invention, will be further described by the following illustrative and non-limiting detailed description of embodiments of the present invention, with reference to the appended drawing(s), wherein:

FIG. 2a-2d illustrates one embodiment for determining at least one modified boundary as disclosed herein, FIG. 5a-5i illustrates one embodiment of morphing between a plurality of scans using the modified boundary as a reference, FIGS. 6a-6c, 7a-7c, 8a-8b, 9, 10a-10b, 11a-11b, 12a-12c, 13a-13c, 14a-14c, 15a-15b, 16a-16c, 17, 18, 19a-19c, 20a-20b, 21a-21b, 22, 23a-23d, 24 and 25, discloses another embodiment of morphing between a plurality if scans, FIG. 26 illustrates a user interface as disclosed herein, and FIG. 27 discloses a processing system for implementing the disclosed method as a computer implemented method.

DETAILED DESCRIPTION

In the following description, reference is made to the accompanying figures, which show by way of illustration how the invention may be practiced.

Figure 1B:
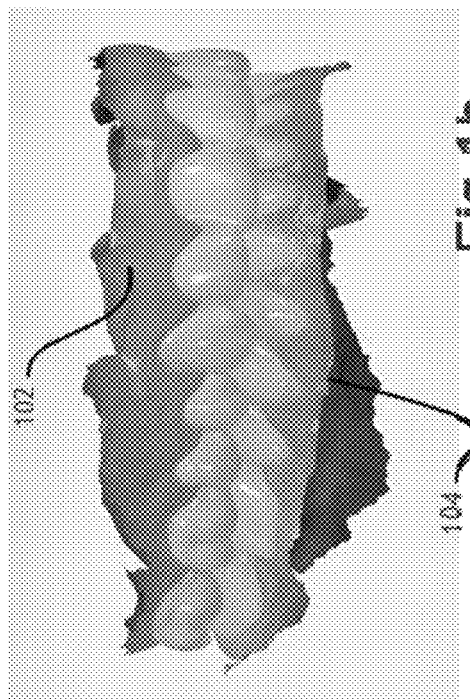
FIGS. 1a and 1b shows two scans taken of a patient at different times.
Figure 1A:
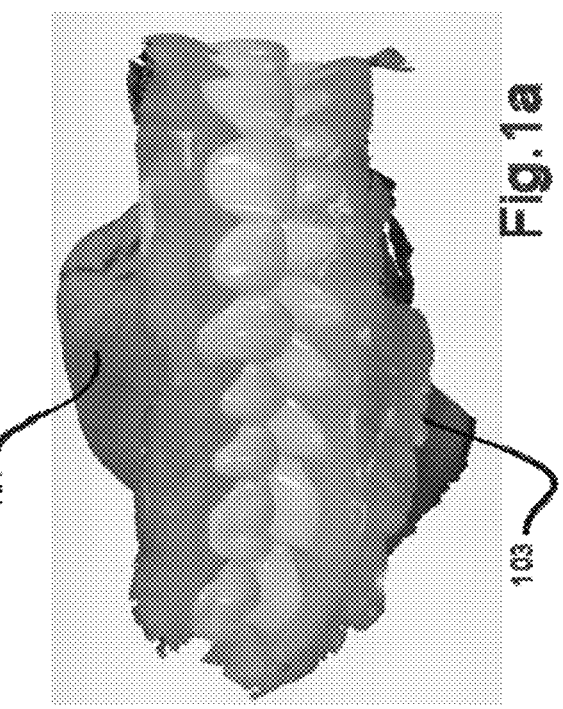

FIGS. 1a and 1b shows a first scan 101 and a second scan 102. The first and second scan has been taken at different times and there is a slight change in the teeth positioning. However, what really catches the visual attention is the scan boundaries 103, 104 of the respective scans. As can be seen these varies substantially and basically depends on when the operator scanning the patient stops scanning and thus do not imply any clinical indication of any sort. Accordingly, when visually presenting the scans in a sequential order as discussed herein the big change in the respective scan boundaries will remove focus from clinically relevant aspects.

One embodiment as discussed herein is shown FIG. 2a-2d, where FIG. 2a shows a first scan 201 of a patient and FIG. 2b shows a second scan 202 of the patient. The first scan 201 and the second scan 202 was taken at different dentist visits where the patient was scanned using an intra oral scanner.

The scan boundary for the first and second scan is determined as the edge of the scan where no scan data is present, which in for the first and second scan results in a first scan boundary 205 of the first scan 201 and a second scan boundary 206 of the second scan 202.

The first and second scans are subsequently transformed into a common coordinate system as shown in FIG. 2c whereby the first scan 201 and second scan 202 overlay each other. This can for example be done practically automatically by using a so-called ICP (Iterative Closest Point) algorithm, which is a method of aligning data that is well known to the person skilled in the art. Alternatively, or additionally, a manual alignment can also be used. This can for example require the user to identify common points on both scans, such as cusps or other dental landmarks.

With the first and second scan arranged in a common coordinate system a modified boundary 207 can be determined as shown in FIG. 2d. In the current embodiment the modified boundary 207 is determined by averaging the first scan boundary 205 and the second scan boundary 206. When doing this, splines are used to define the first and second scan boundary and as a result a spline defining the modified boundary 207 is determined. This modified spline 207' can then be used as a cutting tool for trimming a scan of the patient or as a filling tool defining a boundary to which holes in the scan should be filled by an artificial gingiva texture.

The current embodiment is shown using two scans. Of course, this method can be applied a much higher number of scans than two if needed. In such case the modified boundary will then be created based on an average of all the scan boundaries of the respective scans which are placed in a common coordinate system.

FIGS. 3a to 3f shows another embodiment of presenting a graphical representation of the change of the patients oral situation over time.

Figure 3A:
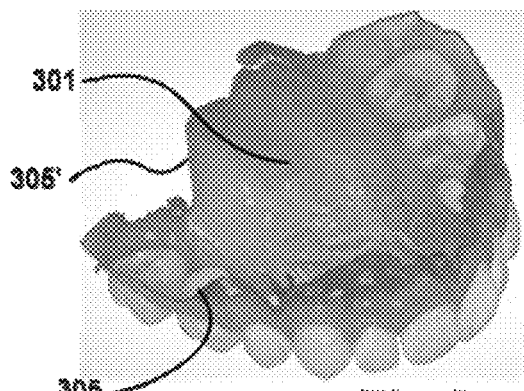
FIG. 3a-3f illustrates another embodiment for determining at least one modified boundary as disclosed herein and how a scan is modified based on the modified boundary.

A first scan 301 is obtained as shown in FIG. 3a. The first scan has a first scan boundary 305, which has been derived into a first scan spline 305'.

Figure 3B:
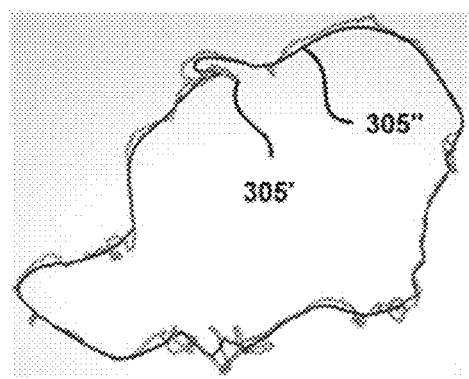
Figure 3C:
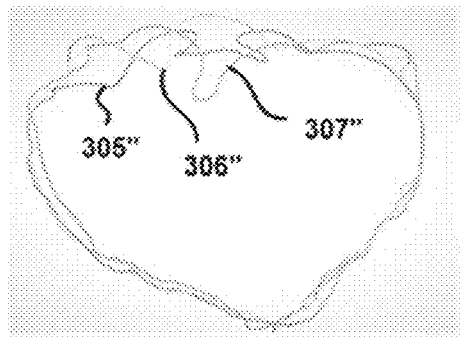

The first scan spline 305' is the linearized by projecting its points to an interpolated line, which generates a first smoothed spline 305" as shown in FIG. 3b.

Figure 3D:
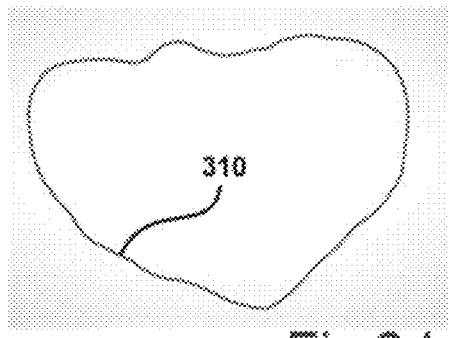

Similar to above additional second and third smoothed splines 306" and 307", shown together with the first smoothed spline 305" in FIG. 3d, are derived from respective second and third scans (not shown) which have been taken at different dentist visits.

The first, second and third smoothed splines 305", 306" and 307" are now averaged to determine a modified boundary in the shape of a modified spline 310 as shown in FIG. 3d.

Figure 3E:
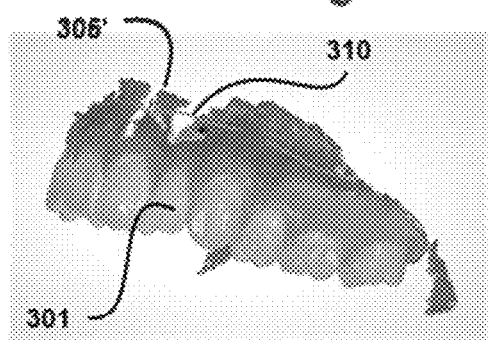
Figure 3F:
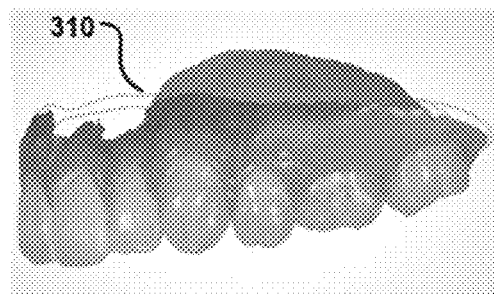

As shown in FIGS. 3e and 3f the modified spline 310 can be used to cut the first scan 305 and also the second and third scan (not shown). This will provide an even and smooth viewing experience as the scans are presented in sequence to illustrate changes in the patients oral situation over time.

Figure 4A:
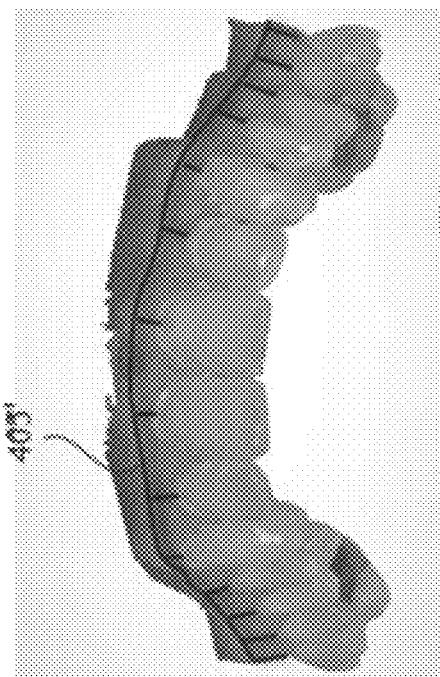
FIG. 4a-4c illustrates yet another embodiment for determining at least one modified boundary as disclosed herein and how a scan is modified based on the modified boundary.
Figure 4C:
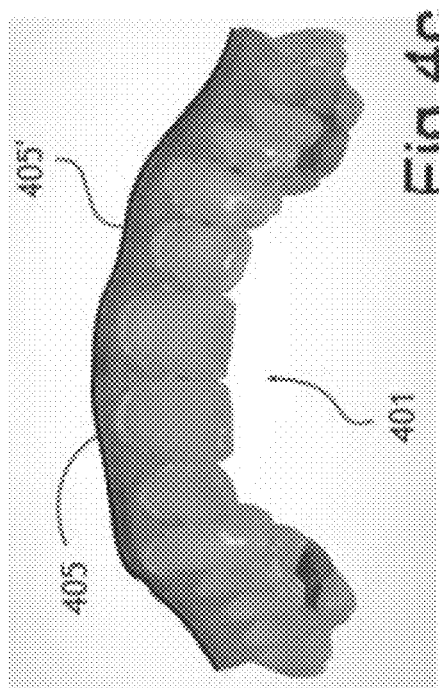
Figure 4B:
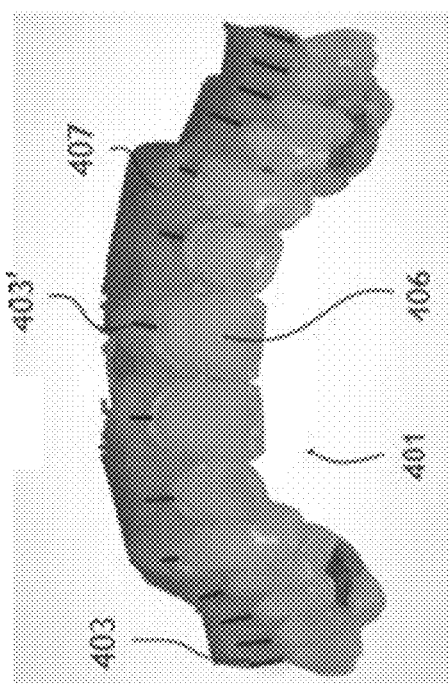

In yet a further embodiment disclosed in FIGS. 4a-4c a reference scan 401 is selected from a plurality of scan and processed in order to determine a modified scan boundary 405. It is disclosed how a modified boundary spline 405' can be determined and used as a cutting spline for trimming a scan 401 of a patient teeth in order to provide the modified scan boundary 405 of the scan where excess scan data has been removed.

In the current embodiment the scan 401 is segmented into teeth 406 and gingiva 407. After segmentation a boundary measurement 403 (for simplicity in the figures not all have been indicated by the reference number) is generated for each tooth. The boundary measurement 403 indicates a certain measure from the respective teeth edges and into the gingiva as shown in FIG. 4a.

In the current example the boundary measurement has been determined by finding a maximum for each tooth and then determine a vertex 403' (for simplicity in the figures not all have been indicated by the reference number), which lies 3 mm into the gingiva from the maximum of the tooth.

The shortest path can then be determined between each vertex 403', e.g. by using the Dijkstra's algorithm. The shortest path between neighboring vertexes defines together the modified boundary spline 405' as shown in FIG. 4b.

The modified boundary spline 405' is subsequently used as a cutting spline for cutting the patient scan 401 in order to remove excess gingiva which is outside the modified boundary spline 405' and thereby generating a modified boundary 405 of the scan 401.

The modified boundary spline 405' is not only used as a trimming or masking tool but is also use as a border for a fill, wherein gaps between the scan 401 and the modified boundary spline 405' is filled with gingiva/soft tissue texture. In another example the boundary spline is not only used as a tool for defining a cut or fill line but is embedded into the surface data in order to create a smooth termination of the scan boundary.

In a related example, the cutting spline is providing the boundary for adding missing data inbetween the spline and the model to create a uniform boundary of the plurality of scans. Adding data may consist of transferring data from the particular region from neighboring models i.e models acquired in close proximity to the model missing some data relative to the spline.

In one example the modified boundary spline is used to remove all data outside of the spline permanently.

In another example, the modified boundary spline is used to define the boundary where all data outside is masked but can be toggled on and off manually according to the wish of the operator—such that all undesired data is invisible when trimming is enabled and original scan data is visible when trimming is disabled.

The modified boundary spline 405' can be used as a reference spline for modifying the scan boundary of a plurality of scans taken at different times from the same patient from which the scan 401 was taken. Alternatively, the modified boundary spline 405' can be used to modify the scan boundary of a group of the plurality of scans taken, it is used for only the one specific scan 401 and a new modified boundary spline is determined for each of the plurality of scans.

In another embodiment (not shown) a plane is fitted to a scan and used as the modified boundary for that scan (or several scans from the same patient. For example, by determining a number of vertexes as described in FIGS. 4a-4c a plane can be fitted using the points as an average. The plane can be displaced if desired before cutting is done.

In an even further embodiment the at least one modified boundary is determined by using a template spline (not shown). The template spline is then used a spline for trimming the plurality of scans so that the scan boundary of the respective scans are modified to a modified boundary using the template spline.

The template spline can be used for all of the plurality of scans, group of the plurality of scans or a single scan from the plurality of scans. Furthermore, different template splines can be used for different scans in the plurality of scans.

For example, the plurality of scans an be divided into groups of scans each group containing scans taken when the patient was within different age ranges. Thus, taking into account that the jaw changes size and shape with age different template splines can be used for the different groups, which thereby takes into account the change in size. The different groups can additionally/alternatively also rely on sex, height, weight or other patient specific data in order to determine the preferred template spline.

It should be understood that determining different modified boundaries for different groups of scans of the plurality of scans and that the groups are generated based on different parameters, such as the age of the patient when scanned, size at the time etc. can be done for all the embodiments described herein.

Alternatively, the same modified boundary can be used for all of the plurality of scans.

Finally, the scans are presented in a time sequence wherein the scan boundary has been modified by the at least one modified boundary spline derived from above process.

In another embodiment as described below with reference to FIGS. 5a-5g the modified boundary is used as a reference for morphing between the plurality of scans in order to provide a simulation of the transition between a set of 'n' segmented jaw meshes (where n is the number of plurality of scans) in a smooth way. Given n consecutive jaw scans, we realize the morphing between them by remeshing all the jaw scans using the same base domain D and generating a sequence R1, R2, . . . , Rk of new regular meshes whose vertex and facet connectivity is identical. It is important to note that we use the segmentation information on the mesh to map corresponding teeth into the exact same region on the base domain.

Segmented scans can advantageously be used since selected segmented structures, e.g. the teeth, can be maintained so that they are not deformed during mapping in any way which ensures that the results can be made highly reliable.

Using pairs of consecutive regular meshes (Ri, Ri+1), we generate the interpolated vertex positions for a value tin [0,1] by taking a vertex v from the regular mesh and combining the vertex position values vi from Ri and vi+1 from Ri+1 using the linear interpolation post(v)=(1−t) vi+t vi+1.

In particular as described in the following, when using the modified boundary to defined the base domain an improved morphing result is achieved.

1. Definition of the Base Domain Using the Modified Boundary.

Figure 5A:
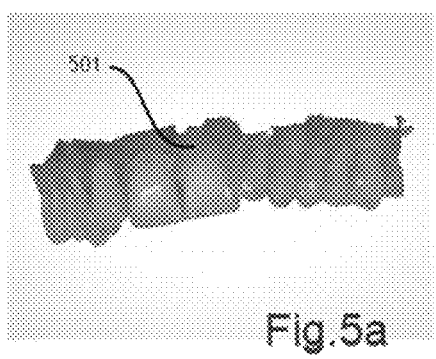
Figure 5B:
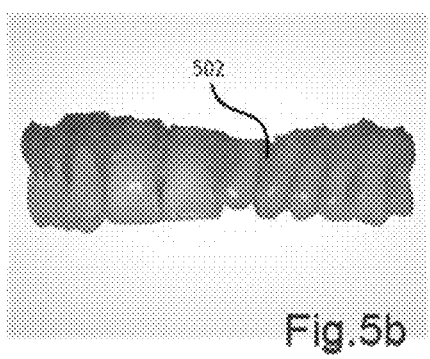

Given n different jaw scans of a patient (i.e. plurality of scans) we first determined a modified boundary as disclosed by one or more of the numerous embodiments disclosed previously herein. FIGS. 5a and 5b shows two (n=2) different jaw scans 501, 502 of the same patient with small displacements in corresponding teeth positions.

Figure 5C:
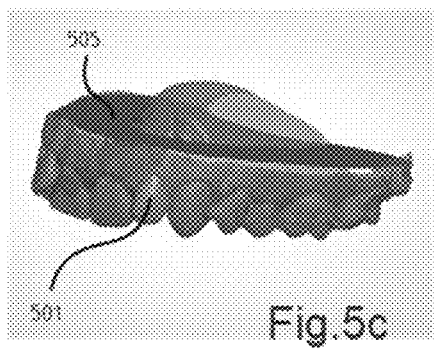
Figure 5D:
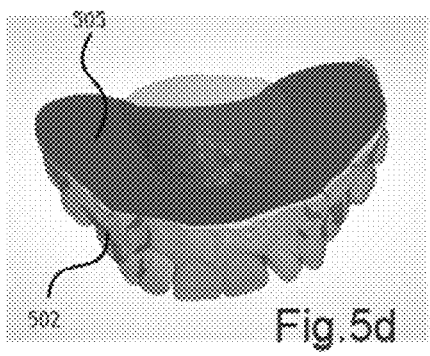

A base domain 505, shown in FIGS. 5c, 5d and 5e is determined by fitting a plane through the modified boundary, defined as an average spline in the current embodiment, and project the modified boundary onto the plane. The base domain is the interior of region on the fitted plane defined by the projected modified boundary. In other words, the base domain is in the current embodiment a 2D surface having a boundary defined by the projected modified boundary.

2. Projection to the Base Domain

Figure 5F:
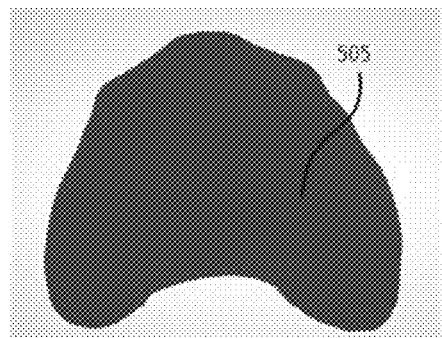

Once the base domain has been defined, the boundary points of the scan boundary of a scan from the plurality of scans is mapped to the closest boundary points on the base domain. In addition or alternatively other constrains can be used, such as the anchor point of the boundary or the teeth as previously discussed. Subsequently a Laplacian mesh processing algorithm is applied in order to obtain a flat representation 510 of the mesh forming the scan as shown in FIG. 5f.

3. Remeshing Using the Base Domain

After the correct base domain and a flattening of the jaw mesh on this domain is obtained a regular mesh is generated with predefined resolution on the base domain.

For each vertex of this regular mesh, one can find the closest corresponding triangle or facet on the flat mesh of the scan and hence calculate a position in 3d space, which lies on the initial jaw scan. Thus, after setting the value of these space point for each vertex of the regular mesh a regularized representation of the scan is obtained.

Figure 5G:
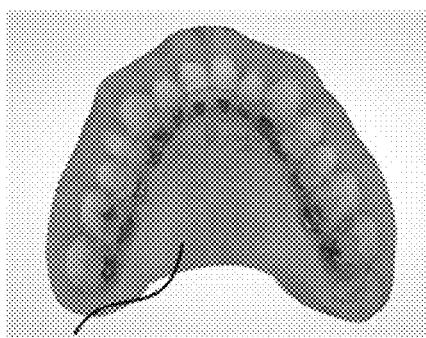
Figure 5H:
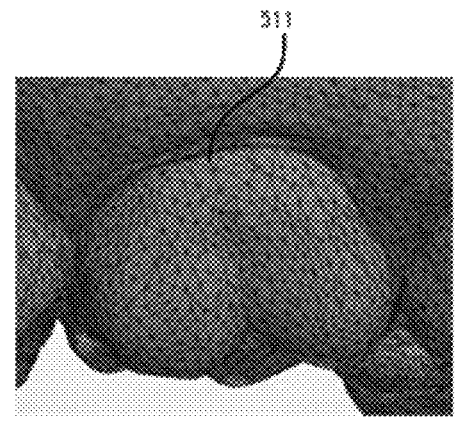
Figure 5I:
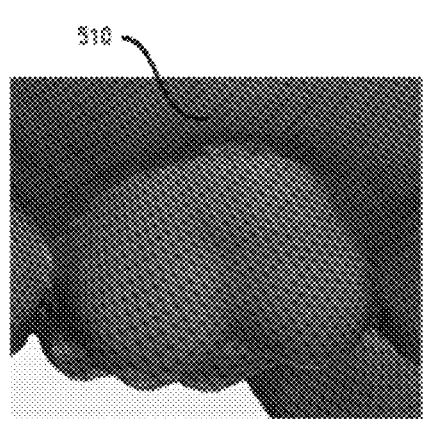

In FIG. 5g it can be seen how the mesh directly taken from the scan 511 is very irregular compared to the regular mesh 512 of FIG. 5h which is applied to the scan in the base domain.

Accordingly, by providing a regularized representation as described above of each of the plurality of scans a one-to-one correspondence of all vertices can be found for all the plurality of scans. This allows for morphing between the scans by providing a linear transformation of the vertices that corresponds to each other.

Another embodiment of applying morphing is laid out in the below steps and discussed in relation to FIGS. 6-31.

The concept and principle of morphing is general known, e.g. from cinematic movies one object changes shape into another object.

In its simplest form morphing interpolates between shapes without any constraints. In this manner if only simple morphing is used for a pair of car models, a car tire can morph into a car door or for a pair of animal models an eye can morph into an ear, which is not correct. This can for example be improved by using feature alignment whereby it is ensured that certain elements in one model morph into a corresponding element in another model making the morphing look more natural.

General morphing principles are well known in the art. For example in the Ph.D. Theses
"Morphing of geometrical objects in boundary representation" by Martina Málková, 2010, University of West Bohemia in Pilsen, Czech Republic
"Morphing of Meshes" by Jindrich Parus, 2005, University of West Bohemia in Pilsen, Czech Republic,
"3D mesh morphing" by Bogdan Cosmin Mocanu, 2010 Institut National des Télécommunications, Paris, France
many morphing principles are discussed.

However, as will be explained in the following, specific improvements have been done in order to optimize morphing between dental setups, e.g. different scans of a patients teeth and gingiva. In particular since we know what is being morphed and we also know that in most cases the morphing is actually done between two identical teeth this knowledge can be used to create highly natural looking morphing as will be explained.

Figure 9:
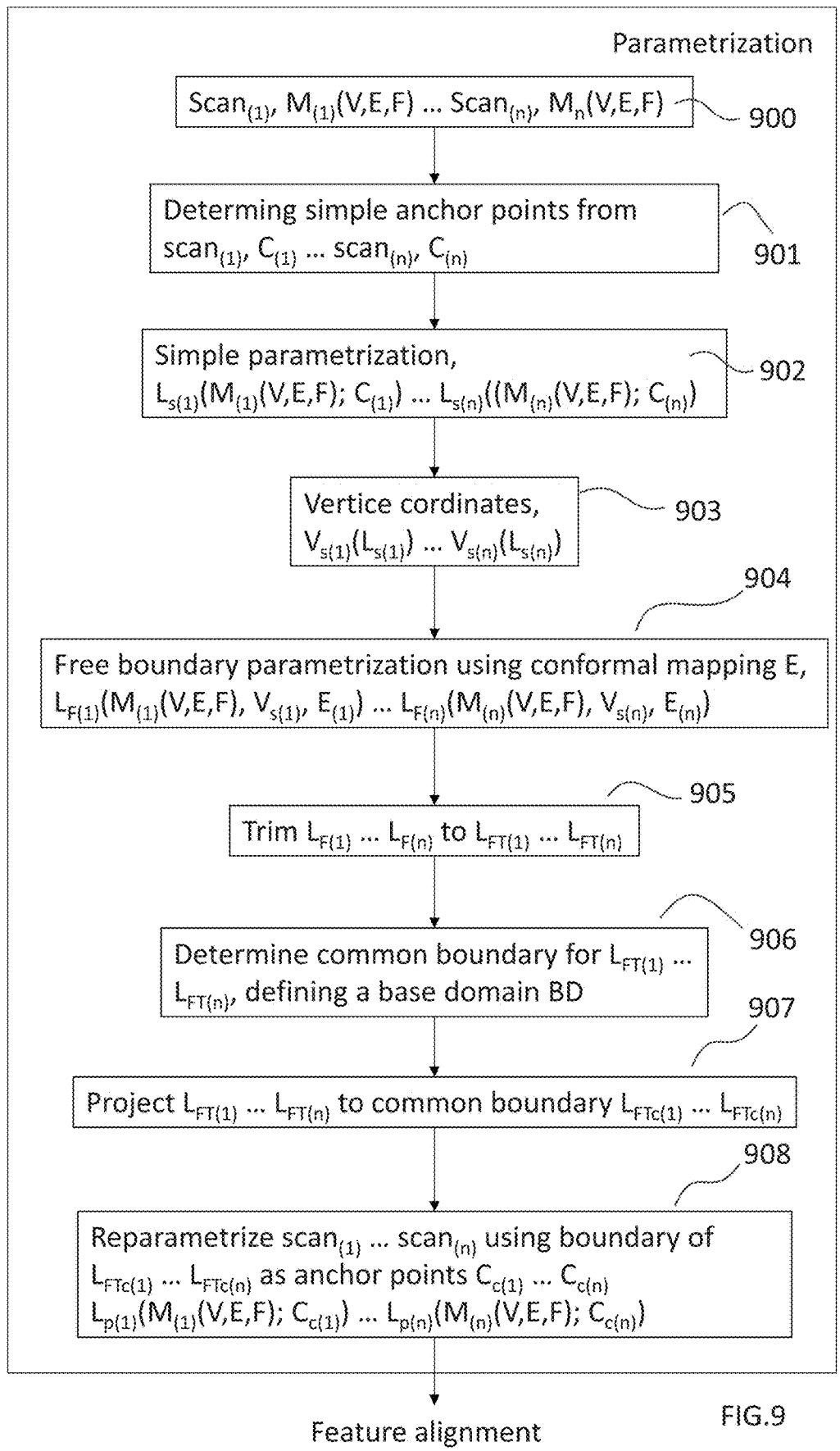
Figure 17:
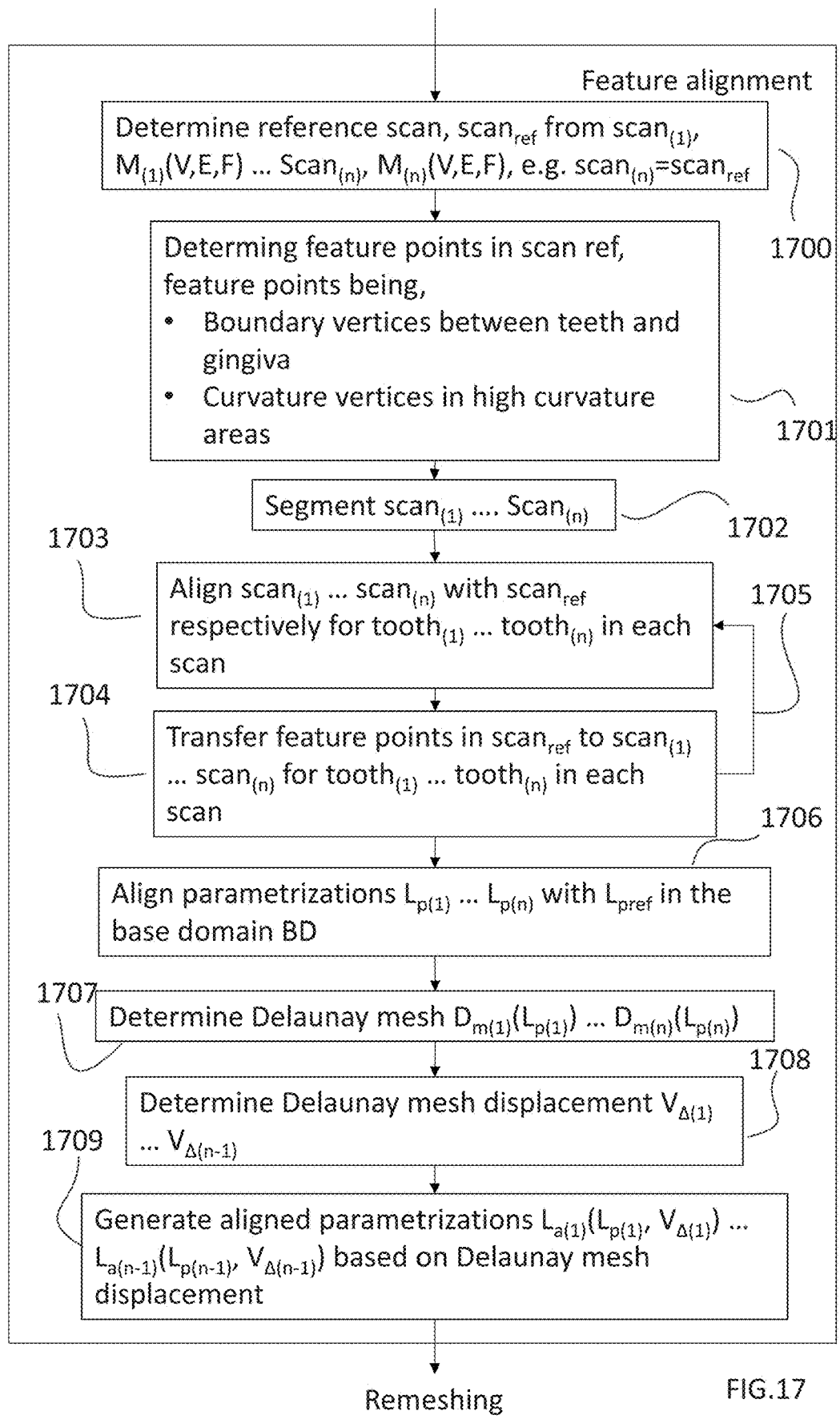

In the following, the morphing has been split up into four processes as illustrated by the respective flowcharts, FIGS. 9, 17, 22 and 25, referred to as the Parametrization process, FIG. 9, Feature alignment process, FIG. 17, Remeshing process, FIG. 22, and Rendering process, FIG. 25.

A substantive part of morphing relates to parametrization as will also be discussed. However, the calculations of mesh parametrization involve iterative solution of large sparse linear equations, the time complexity of these algorithms is cubic in the number of vertices. This practically means that for real scans with 100.000+ vertices as shown in FIG. 6b the time it takes to solve the linear systems is inacceptable.

Figures 6A, 6B, 6C:
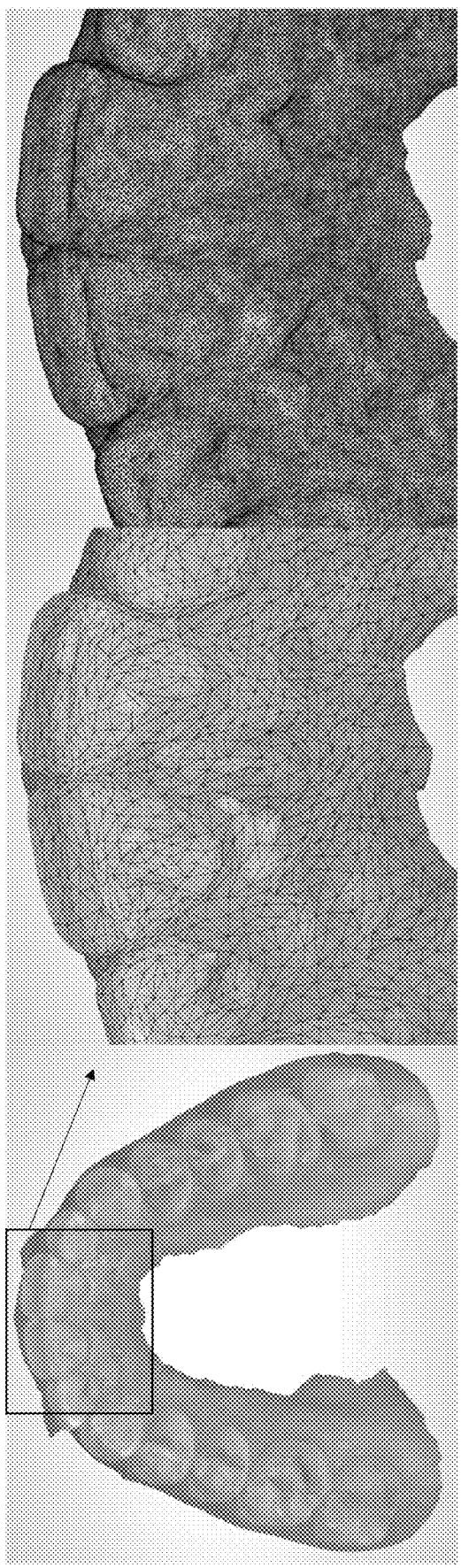
Figures 7A, 7B, 7C:

Thus, although not necessary for the function of the process but in order to speed up processing speed the scans can advantageously be decimated the number of vertices be reduced to 10-15.000 as shown in FIG. 6c and do the parametrization operations on these low-resolution meshes which results in a low resolution parametrization as shown in FIG. 7b.

Subsequently the parametrization is transferred to the original scans using barycentric mapping which provides the high resolution mesh shown in FIG. 7c. This technique of using two copies of the same mesh with different resolutions in the solution of problems is called multi resolution mesh representation.

Figure 8B:
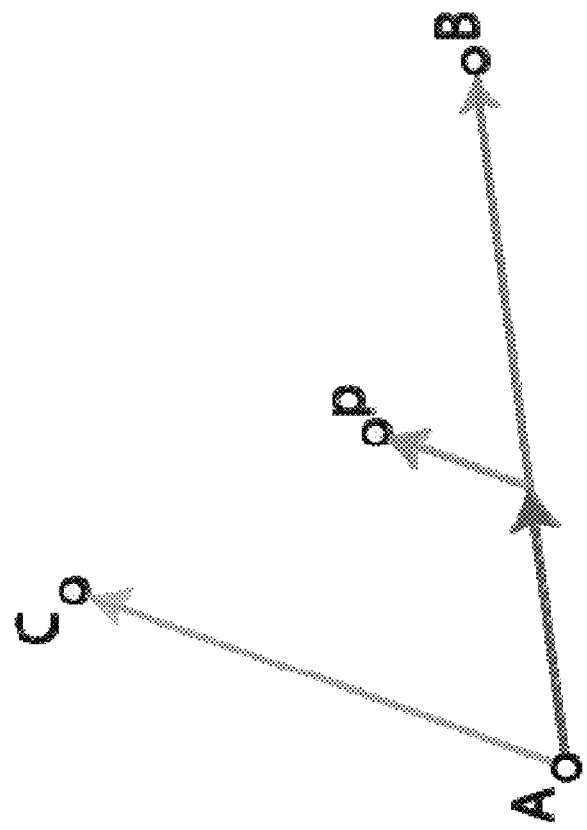
Figure 8A:
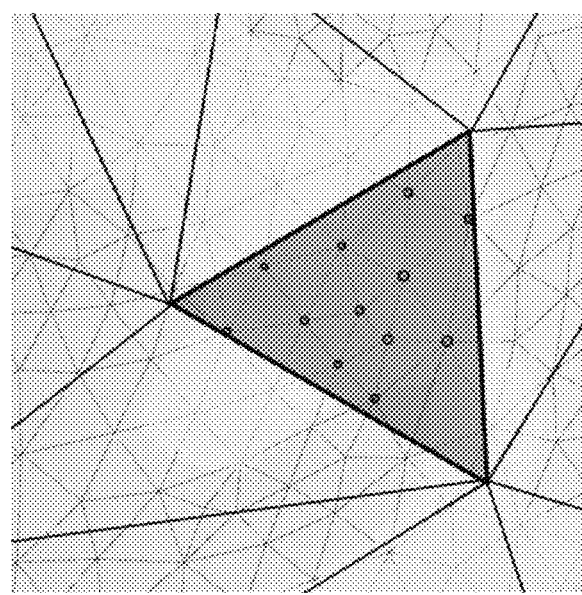

In FIG. 8a it is shown how vertices 80 from the higher resolution mesh are mapped to points inside a facet 81 of the lower resolution mesh.

FIG. 8b shows the barycentric coordinates that are representations of a point p inside of a triangle ABC as a linear combination of the vectors AB and AC of its sides. Based on this knowledge the barycentric mapping can be performed and a low resolution mesh can be used to perform CPU intensive calculations and processing. Afterwards the barycentric mapping is used to transfer the result to a higher resolution mesh. Barycentric mapping may also be used in other process steps as will be discussed in the following.

Process 1, "Parametrization"

In a first step a common parametrization defined by a base common/base domain for all meshes is generated. It comprises of several parametrization sub-steps as will be discussed in the following with reference to the workflow in FIG. 9 and the images in FIGS. 10-16.

Parametrization is a generally known concept within 3D graphics and basically relates to mapping the 3D models to be morphed into a common geometric domain. This can for example be done by projecting the 3D models to a common sphere, disc, 2D plane or possibly a region in a 2D plane defined by a boundary. The parametrization is then used to find correspondences between respective vertices of the 3D models. These correspondence are then used to calculate the rendering of the intermediate states of the 3D models when playing the morphing on the monitor.

In step 900 a number of scans, $scan_1 \ldots scan_n$, are obtained. Each scan is represented by a mesh M represented by vertices V, edges E and faces F, i.e. $M_{(1)}(V,E,F) \ldots M_{(n)}(V,E,F)$ respectively. The scans can for example be obtained by intra-oral scanning using a TRIOS scanner manufactured by 3shape TRIOS. FIG. 10a shows a scan 90 represented by a mesh M, although the mesh is not visually shown in the figure.

In order to parametrize the respective scans, control points (also called anchor points) needs to be defined. In step 901 control points $C_{(1)} \ldots C_{(n)}$ for $scan_{(1)} \ldots scan_{(n)}$ are set on the boundary of the respective scan meshes when viewed from the occlusal side. In FIG. 10a it is seen how the control points 91 are placed along the boundary when the scan is seen from an occlusal view.

In step 902 Laplacian mesh processing is used to generate simple parametric representations of the jaw meshes $L_{s(1)}(M_{(1)}(V,E,F), C_{(1)}) \ldots L_{s(n)}(M_{(n)}(V,E,F), C_{(n)})$. This process calculates optimal positions for mesh vertices by using the fixed anchor points 91 and solving a linear least squares equation generated from the mesh geometry and the anchor points.

Simple parametrization uses the boundary vertices of a jaw mesh and fits a plane as the geometric domain on them and projects all the boundary vertices on this plane. Solving the Laplacian equation for these anchor points gives the simple plane parametrization.

As can be seen in FIGS. 10a and 10b the 3D jaw mesh 90 (M) in FIG. 9a has been parameterized to a plane (flattened) in FIG. 9b generating a parameterized mesh 90' (M').

This method of mesh parametrization is very simple and efficient, however, it has the downside that because of the arbitrariness of the anchor points there may occur problems in the mapping of the boundary which have negative impact on further steps.

Figure 11B:
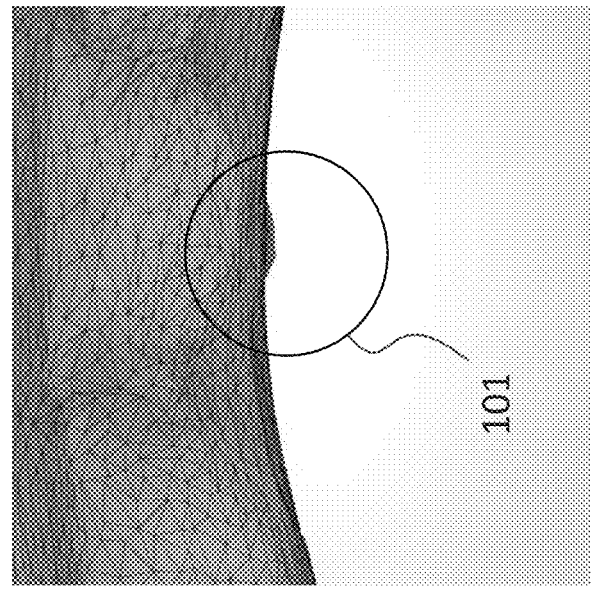
Figure 11A:
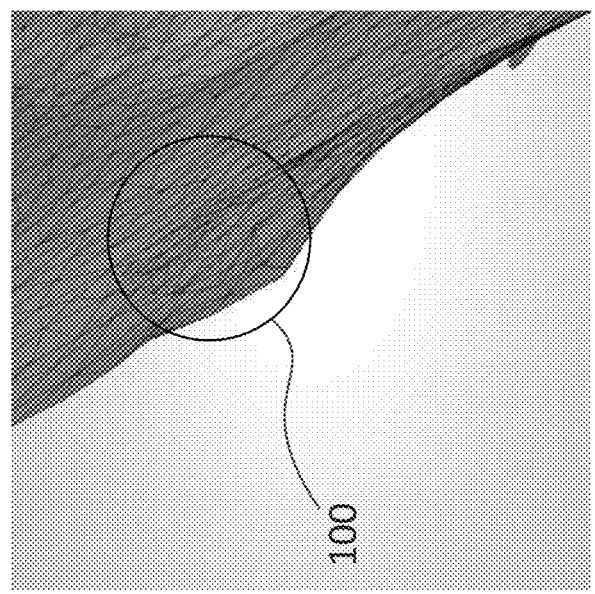

For example, when looking at the meshes 90 and 90' in FIGS. 11a and 11b the boundary of the meshes are very similar. However, due to the simple parametrization using the anchor points 91 as explained above the meshes at the boundary often creates conflicts such as overlapping meshes 100 in FIG. 11a and/or highly concentrated and stretched out meshes 101 shown in FIG. 11b.

This simple mesh parametrization is still useful, because the coordinates of the vertices for each mesh $V_{s(1)} \ldots V_{s(n)}$ determined in step 903 are used to perform an improved parametrization in step 904.

In order to handle the errors created by the simple parametrization in step 902 an improved parametrization the jaw meshes using quasi-conformal mapping E is performed in step 904 referred to as a free boundary parametrization $L_{F(1)}(M_{(1)}(V,E,F), V_{s(1)}, E) \ldots L_{F(n)}(M_{(n)}(V,E,F), V_{s(n)}, E)$.

The quasi-conformal mapping of the jaw mesh generates a free boundary parametrization into the geometric domain which minimizes the Dirichlet or conformal energy of the mesh.

A conformal map is a function that locally preserves angles and orientations. In our case we use a mapping that minimizes the angle and length distortion or in other words preserves them as good as possible. This type of conformal mapping is also referred to as quasi-conformal. In the current embodiment the free boundary parametrization is generated by taking a simple parametrization of the mesh, such as the one used in step 902, and solving the same Laplacian linear system with the modified constraint that the gradient vector fields of our new parametrization are "as orthogonal as possible".

FIGS. 12a, 12b and 12c show examples of such conformal maps, where FIG. 12a shows a uniform quad mesh and FIGS. 12b and 12c show examples of their conformal mappings.

After solving the linear system representing the quasi conformality constraint the free boundary parametrizations $L_F$ of the jaw models are obtained, which in the given sense have as natural as possible boundary representations on the plane.

Figure 13C:
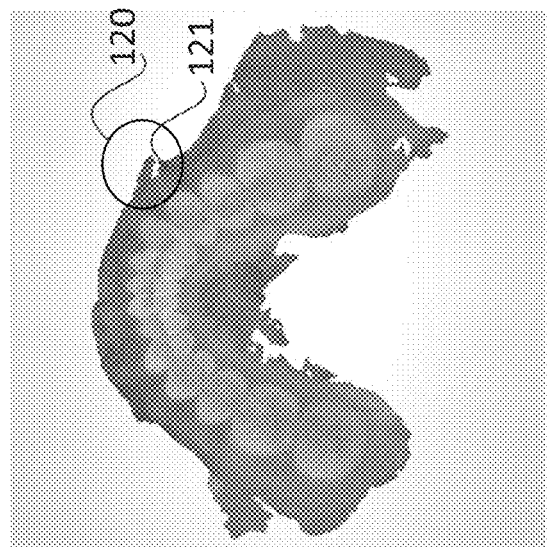
Figure 13B:
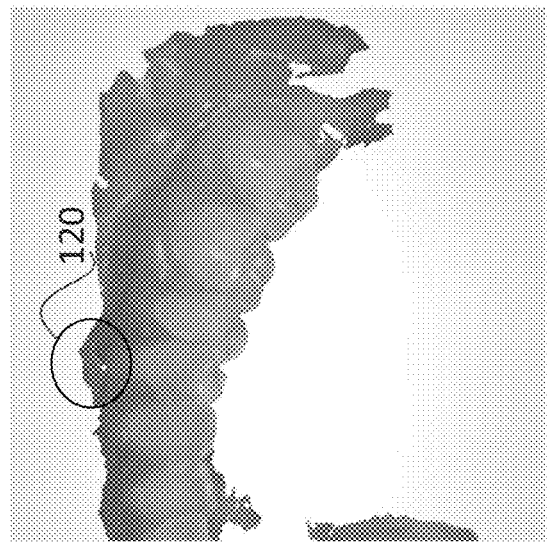
Figure 13A:
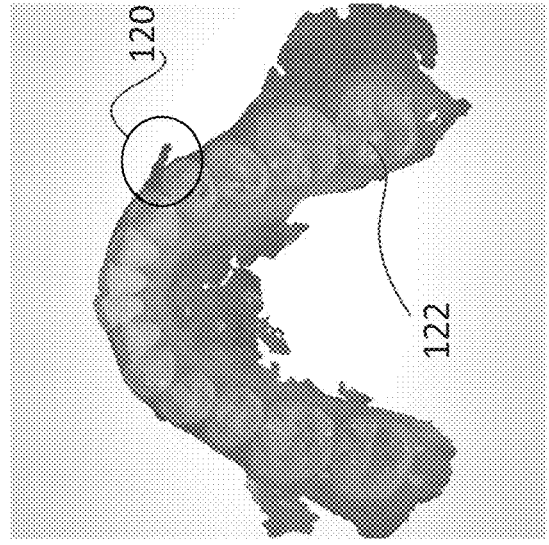

For example a 3D jaw mesh 122 is shown in FIG. 13a. However, as can be seen in FIG. 13b protrusion 121 in area 120 is mapped in a natural way on the plane and preventing e.g. overlapping mesh data.

If desired these parametrizations can now be used to generate the common parametrized domain (base domain BD) for the jaw scans as discussed in step 906. However, since the irregularities on the gingiva boundary are not relevant for the simulation, we will use these parametrizations to remove/trim excess gingiva from the initial models $L_{F(1)} \ldots L_{F(n)}$ in step 905. This will considerably simplify the logic for handling of boundary irregularities, as we will be able to assume that the input models have regular and smooth boundaries.

Figure 14C:
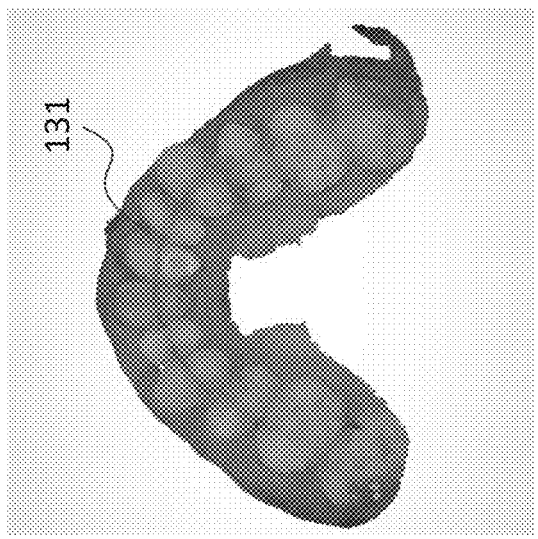
Figure 14B:
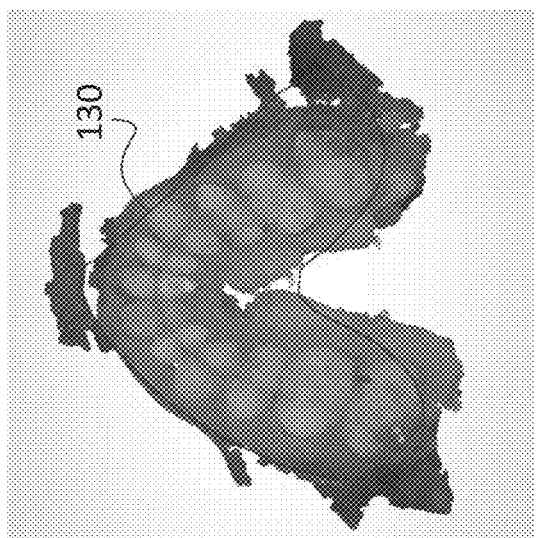
Figure 14A:
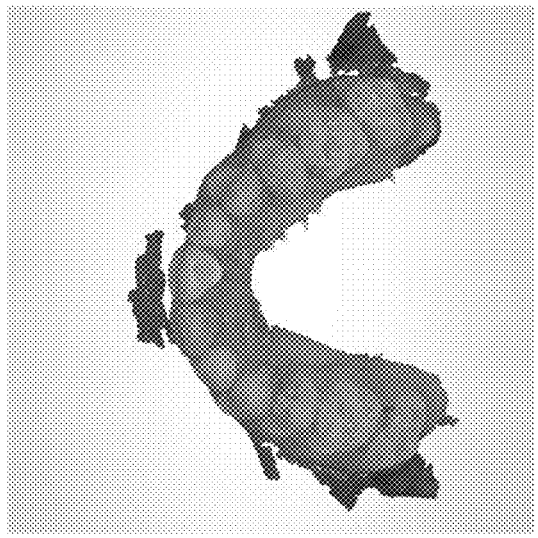
Figure 15B:
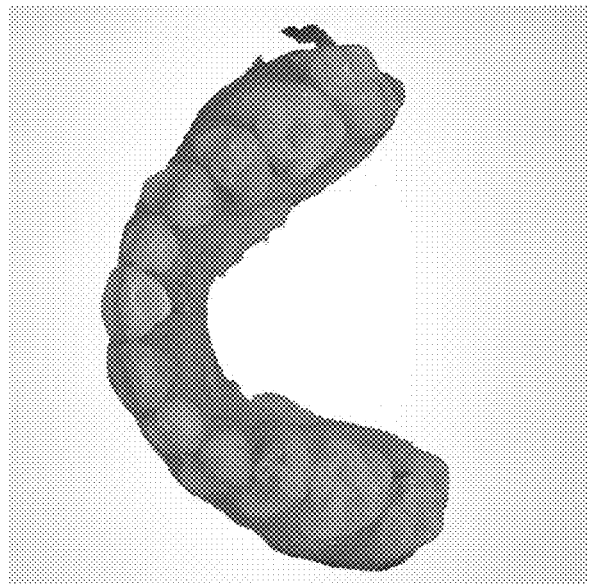
Figure 15A:
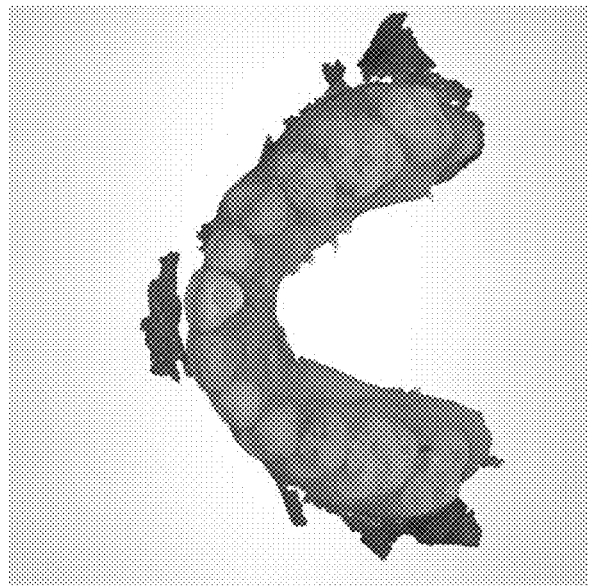

After having obtained a free boundary parametrization, one generates a spline 130 from its boundary as shown in FIG. 14b and runs a series of spline simplification and smoothing algorithms on it. By discarding the mesh facets that lie outside of this spline 130 a trimmed parametrization 131, $L_{FT(1)} \ldots L_{FT(n)}$ is obtained as shown in FIG. 14c. It is important to note that if no constraints are put to the spline simplification algorithms, in some cases the resulting spline can remove some tooth facets as is seen in the FIG. 14b. A specific check for this can be done so that facets that belong to teeth segments are kept.

Figure 16C:
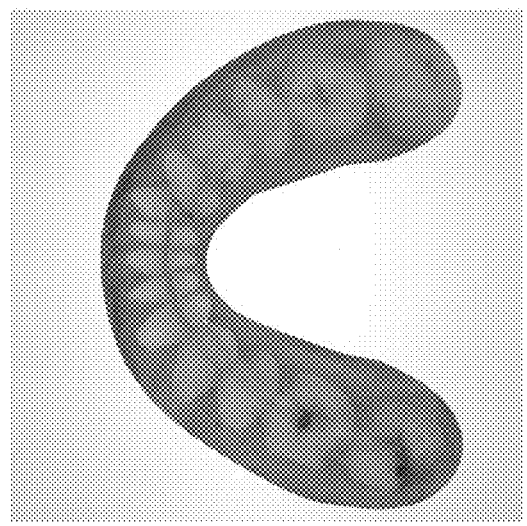
Figure 16B:
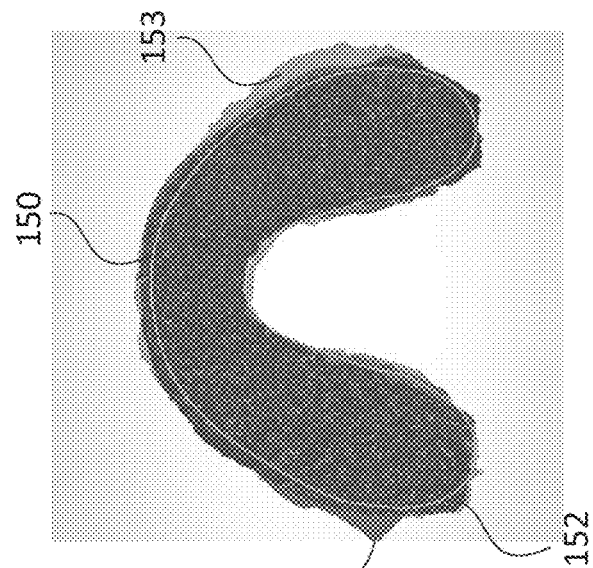
Figure 16A:
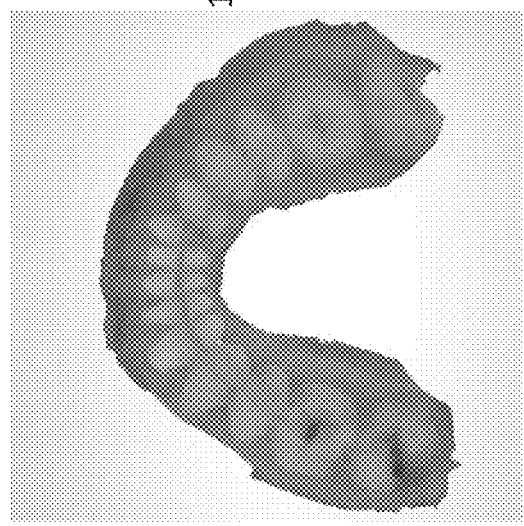

In step 906, and as shown in FIG. 16b a common boundary 150 is determined. After processing the scans, $scan_{(1)} \ldots scan_{(n)}$, as described above from step 900 to step 905 a common boundary 150 for the parametrized models, $L_{FT(1)} \ldots L_{FT(n)}$, can be determined.

The free boundaries 151, 152 and 153 of the parametrized models are used to determine the common boundary 150 as an average. The common boundary 150 thus defines the boundary of the base domain BD to which all the parametrizations of the scans, $L_{FT(1)} \ldots L_{FT(n)}$, will be fitted. The reason why this boundary is used for common parametrization is because in a mathematical sense it represents the most natural common boundary to use for parametrizing all input models at once. This selection of a natural boundary ensures that all models are mapped to the same common boundary with minimum average distortion of the facets.

The boundary points of the parametrized meshes, $L_{FT(1)} \ldots L_{FT(n)}$, are subsequently projected to the common boundary of the base domain BD in step 907 thereby generating parametrizations $L_{FTC(1)} \ldots L_{FTC(n)}$ which all have the same boundary.

Finally the scans, $scan_{(1)} \ldots scan_{(n)}$, are reparametrized in step 908 wherein the projected boundary for each corresponding parametrization $L_{FTC(1)} \ldots L_{FTC(n)}$ in step 907 are used as anchor points $C_{c(1)} \ldots C_{c(n)}$ for the Laplacian re-parametrization, thus generating reparametrizations $L_{P(1)}$ $(M_{(1)}(V,E,F), C_{c(1)}) \ldots L_{P(n)}(M_{(n)}(V,E,F), C_{c(n)})$. With this input the algorithm produces the desired common boundary parametrizations which are minimally distorted.

Step 2, "Feature Alignment"

Above step 1 is basically an alternative to the parametrization described for steps 1 above with respect to FIGS. 5a-5g, where rendering the morphing subsequently can be performed based on the parametrizations. However, in order to improve the morphing, input can be provided that ensures that relevant features are morphed to corresponding features in the other scans by using the feature alignment as disclosed with respect to step 2 herein.

In particular, seeing that we are working with dental movement and assume that all the scans are taken from the same patient over time we can apply the knowledge that the morphing is not done between completely different models, but instead morphing is done between jaws wherein we expect to find teeth that correspond to each other in shape even if there is change over time. As will be discussed in the following, this knowledge is relevant for the feature alignment in step 2, but also for the remeshing in step 3 and rendering in step 4 and thus creates a morphing process which is different from other morphing approaches since the process takes into account this assumed knowledge of the teeth.

Accordingly, in order to get a realistic morphing experience, the corresponding features in the current embodiment of individual teeth and gingiva are aligned and overlapped in the parametric domain. If a tooth is aligned with gingiva or vice versa, then the tooth will morph into gingiva and vice versa.

To start the feature alignment we select one parametrized model $L_{pref}$ from the parametrized models $L_{p(1)} \ldots L_{p(n)}$ as the reference model $scan_{ref}$ in step 1700, $M_{ref}(V,E,F)$ and will subsequently align all the other models to this. In the current embodiment we chose the parametrized model of the latest scan $L_{p(n)}$, $scan_{(n)}$ as the reference model, $L_{pref}=L_{p(n)}$. The other parametrizations $L_{p(1)} \ldots L_{p(n-1)}$ will accordingly be the parametrizations that will be aligned to the reference parametrization.

In the subsequent step 1701, FIG. 18, feature points 1600, 1601 are identified in the 3 model 1602 of the reference scan, $scan_{ref}$. In the current embodiment the feature points are identified by looking for two types of vertices in the 3D model, 1) Boundary vertices 1600 between teeth and gingiva, and
2) Curvature vertices 1601 in high curvature areas of teeth and gingiva The curvature measure used is the mean discrete curvature at a given vertex. It is calculated using the average of the minimal and maximal discrete curvature on a vertex.

Subsequently, in step 1702, we segment the teeth in the scans $scan_1 \ldots scan_n$. Tooth segmentation are generally known within the digital dentistry and can be done manually by having the user identify teeth, however, automatic segmentation have also become commonplace by using e.g. image recognition and also deep learning.

The segmentation is used to align each of the teeth in the scans $scan_{(1)} \ldots scan_{(n-1)}$ with each corresponding tooth in reference scan, $scan_{ref}$, in step 1703.

For each tooth align between a scan from the scans $scan_{(1)} \ldots scan_{(n-1)}$ and the reference scan, $scan_{ref}$, corresponding feature points are transferred from that tooth in the reference scan to the corresponding aligned tooth in the aligned scan in step 1704 by transferring the feature vertices to each model by calculating tooth to tooth alignment and then finding the closest point.

Seeing that each tooth may have moved differently it may be necessary to iteratively do the alignment for each tooth as described above instead of aligning the full scans. Accordingly, an iteration step 1705 is done in order to correctly align each tooth from all the scans $scan_{(1)} \ldots scan_{(n-1)}$ to the reference scan, $scan_{ref}$, as discussed in step 1703 and transferring the feature points for each alignment as discussed in step 1704. This ensures that boundary 1600 vertices are mapped to corresponding boundary vertices and landmark (curvature) 1601 vertices to corresponding landmark vertices for each tooth separately. A good morphing should map these vertices with the highest possible accuracy to be perceived as realistic. Otherwise unnatural deformations in the transition between models may occur.

Figure 19A:
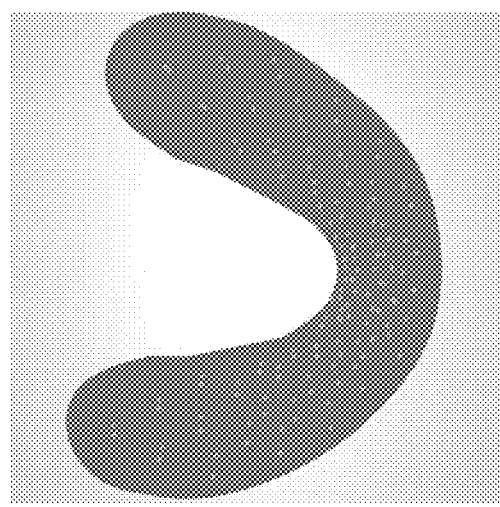
Figure 19B:
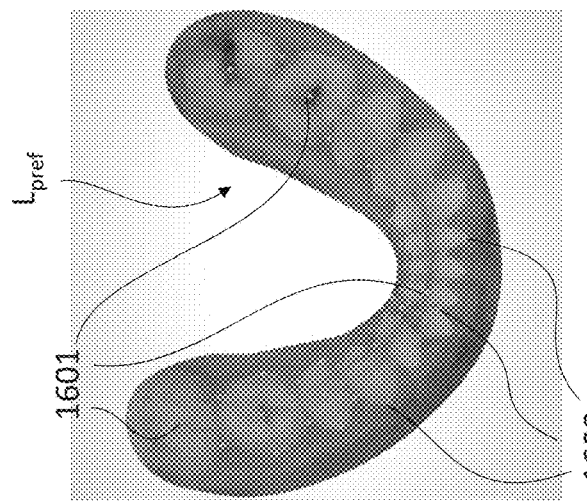
Figure 19C:
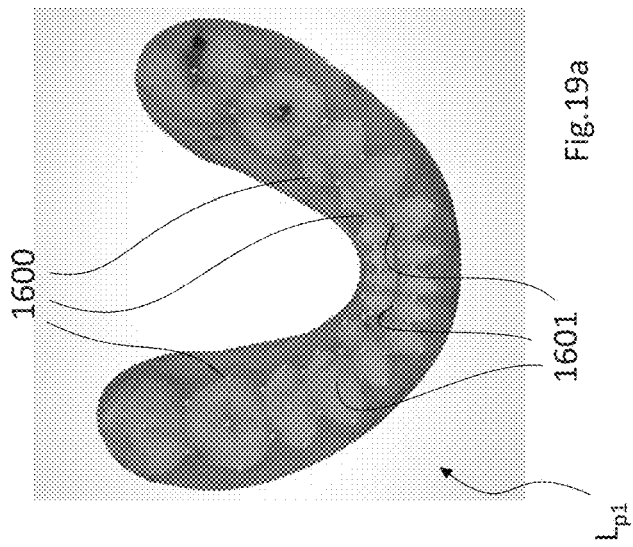

FIG. 19a shows the feature points mapped on one parametrized model $L_{p(1)}$ and FIG. 19b shows the feature points mapped on the reference parametrization $L_{pref}$. With all the identified feature points 1600, 1601 transferred to each of the scans $scan_{(1)} \ldots scan_{(n-1)}$ the parametrizations $L_{p(1)} \ldots L_{p(n-1)}$ are subsequently aligned with the reference parametrization $L_{pref}$ in step 1705 and shown in FIG. 19c.

Figure 20B:
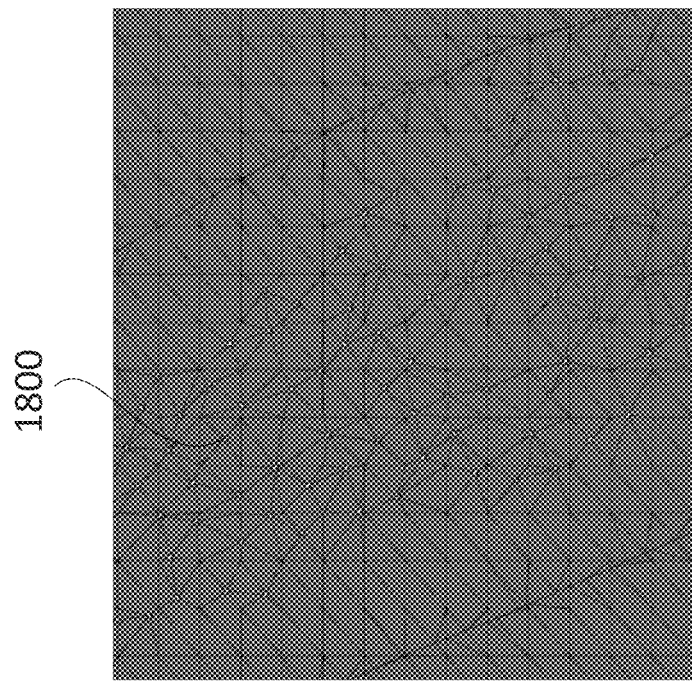
Figure 20A:
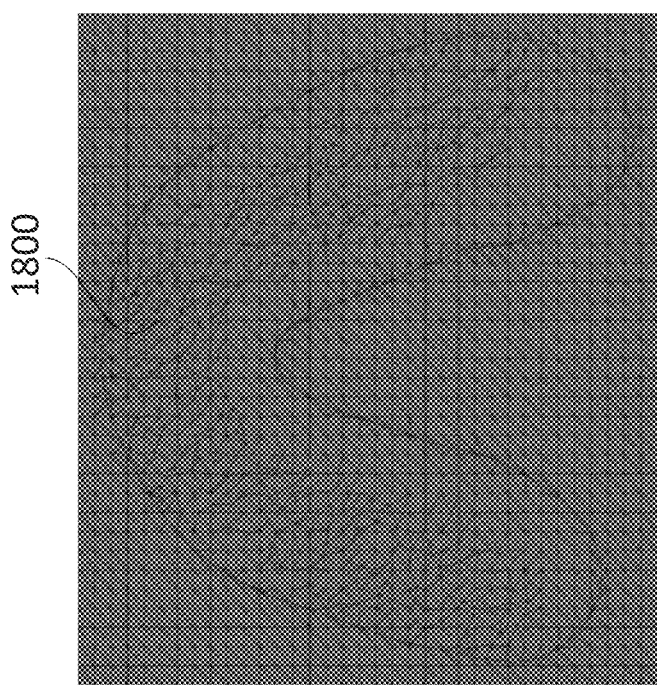

In step 1706 a Delaunay mesh is generated for each of the parametrizations $D_{m(1)}(L_{p(1)}) \ldots D_{m(n)}(L_{p(n)})$, $D_{m(n)}=D_{mref}(L_{pref})$. This is done by generating a regular square mesh and appending all the feature points to it using Delaunay triangulation. Delaunay triangulation itself is well known in the art and is used to maximize the minimum angle of all the angles of the triangles in the triangulation. This creates a plane mesh consisting of feature points 1800 as shown in FIGS. 20a and 20b.

Subsequently, in step 1707, displacements of the Delaunay meshes are generated. This is done by pairing each of the meshes $D_{m(1)}+D_{mref} \ldots D_{m(n-1)}+D_{mref}$. For each pair we displace the Delaunay mesh without generating flip-overs using the target positions of the feature vertices in order to determine the displacement for each vertice $V_{\Delta(1)} \ldots V_{\Delta(n-1)}$ in the respective Delaunay mesh $D_{m(1)} \ldots D_{m(n-1)}$ relative to the reference mesh $D_{mref}$.

Figure 21B:
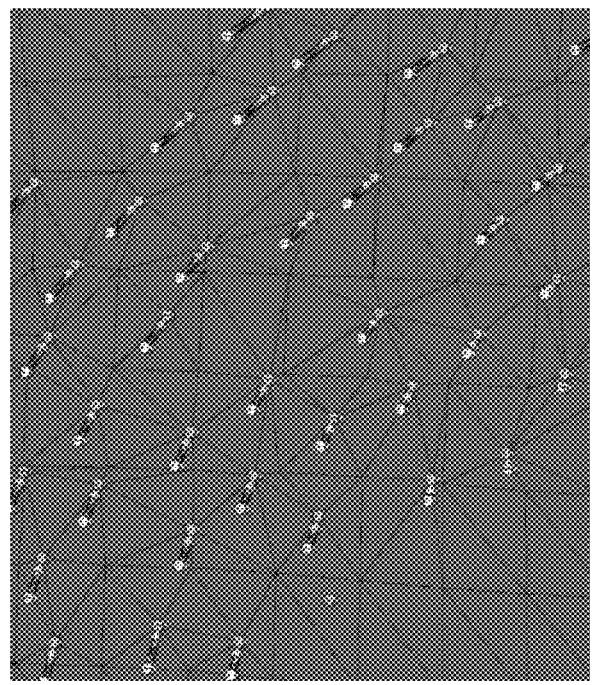
Figure 21A:
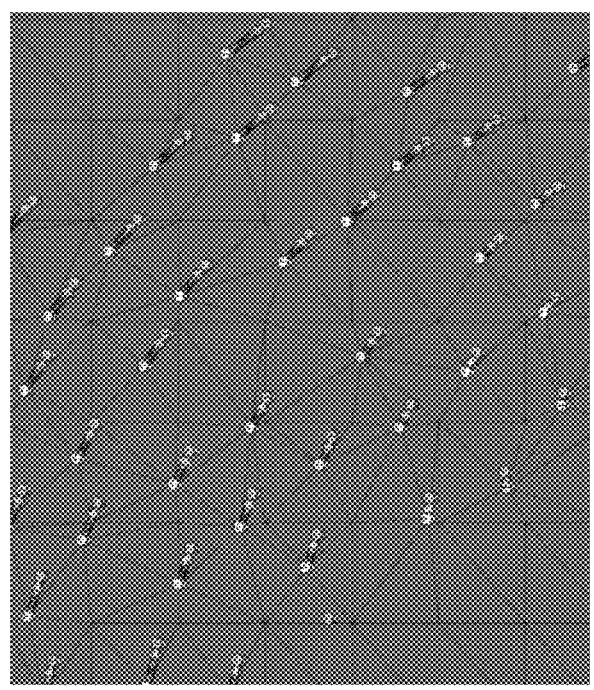

As the Delaunay mesh has more vertices than the feature vertices we use Laplacian mesh processing in order to interpolate optimal positions for all the vertices given the target positions of feature vertices as a constraint. FIGS. 21a and 21b show enlarged sections of an exemplary mesh showing such displacement where the arrows shows the direction of movement of the feature vertices.

Finally, the feature alignment is completed by transferring the displacement $V_{\Delta(1)} \ldots V_{\Delta(n-1)}$ to the parametrized meshes $L_{p(1)} \ldots L_{p(n-1)}$ to generate aligned parametrizations $L_{a(1)}(L_{p(1)}, V_{\Delta(1)}) \ldots L_{a(n-1)}(L_{p(n-1)}, V_{\Delta(n-1)})$ in steps 1708 and 1709.

Using barycentric mapping and the pair of the two feature meshes the aligned parametrized model $L_{a(1)} \ldots L_{a(n-1)}$ can be generated where the teeth projections are aligned to the reference mesh.

This is achieved in the following way. A vertex v from a parametrized mesh $L_{p(1)}$ is mapped to its corresponding facet f and its barycentric coordinates are calculated in the Delaunay mesh $D_{m(1)}$. Using the vertex displacements $V_{\Delta(1)}$, this facet from the Delaunay mesh is displaced to its target position f'. The new position v' is calculated using barycentric coordinates for the displaced facet f'. In this way the segments of $L_{a(1)}$ are aligned as precise as possible with the segments of the reference mesh $L_{pref}$.

Accordingly, all the parametrizations have now been aligned based on their features. Bear in mind, that due to the nature of parametrization the original 3D model is maintained via the transformation even though the parametrization have been modified. This is one of the strength of working with parametrizations instead of the 3D models themselves and is used to an advantage in the current embodiment in order to ensure that the identified feature points 1600, 1601 in the $scan_{ref}$ are transferred over to each of the scans $scan_{(1)} \ldots scan_{(n-1)}$ with high accuracy.

Figure 22:
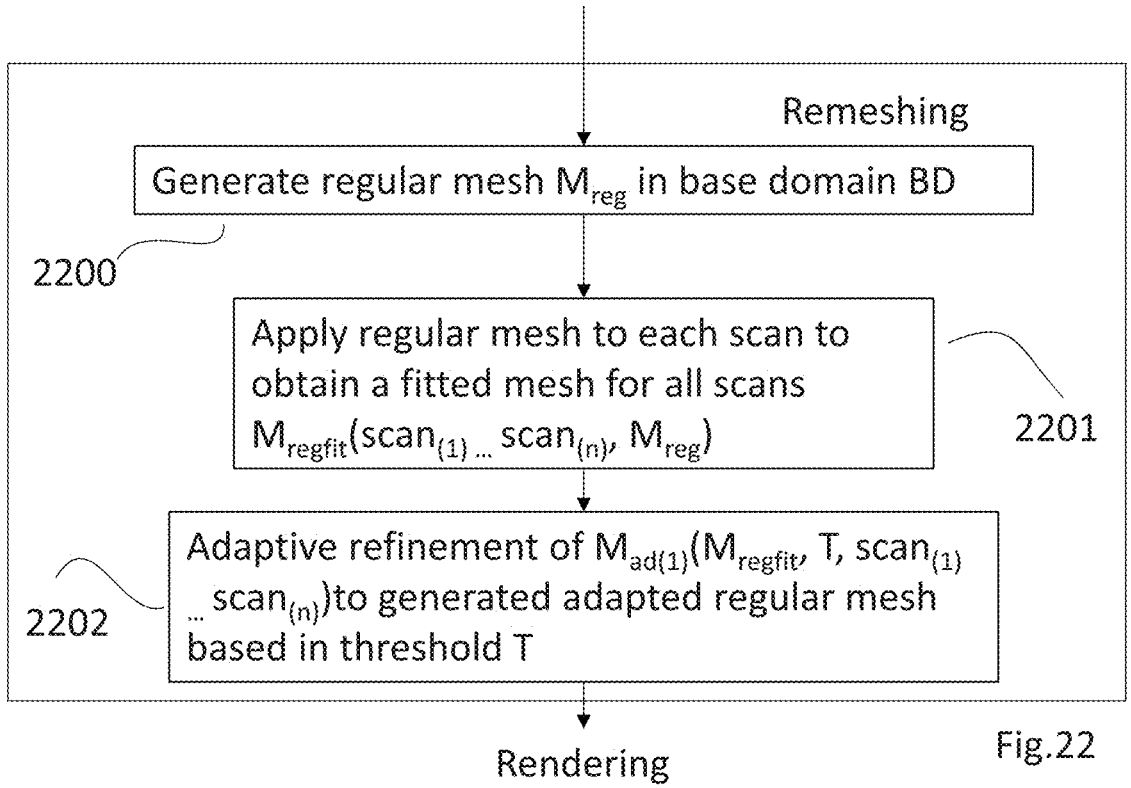

In step 3 a remeshing is performed by generating a regular mesh with adaptive refinement as shown in FIG. 22. Seeing that each of the scans $scan_{(1)} \ldots scan_{(n)}$ have their own different meshes there is not a one-to-one correspondence between each vertex of the scans.

Although the mesh of the reference model can be used as a reference mesh for the other meshes it may be an advantage to provide a regular mesh that can be used as this will provide a better reference mesh across all models and thus also determine closest corresponding points. Advantageously, by applying the same adapted regular mesh to all of the scans an even more natural and uniform morphing can be generated.

After the correct base domain and a flattening of the jaw mesh in the base domain has been obtained a regular mesh 2301, $M_{reg}$, as shown in FIG. 23, with predefined resolution is generated on the base domain BD as shown in step 2200.

In step 2201 the regular mesh $M_{reg}$ is fitted to the scans $scan_{(1)} \ldots scan_{(n)}$. Using barycentric mapping as explained previously, the vertices of the regular mesh are mapped to their positions in 3d space corresponding to the scans. The corresponding texture u-v coordinate is determined and the texture is mapped.

For each vertex of this regular mesh, the closest corresponding triangle on the parametrized mesh can be determined and a position in 3d space that lies on the initial jaw scan can be calculated. After setting the value of these space points for each vertex of the regular mesh the regularized representation of all the scans is obtained in one regular fitted mesh $M_{regfit}(scan_{(1)} \ldots scan_{(n)}, M_{reg})$.

Finally, in step 2202, and adaptive refinement of the base domain with respect to a threshold T is performed $M_{ad(1)}(M_{regfit}, T, scan_{(1)} \ldots scan_{(n)})$ fitting the mesh to accommodate for any irregularities that may still be present between the aligned meshes $L_{a(1)} \ldots L_{a(n)}$.

The simple regular base jaw is not suitable for a high-quality re-meshing, because it does not differentiate between regions of high curvature, where a higher resolution and regions of low curvature is needed, where lower resolution does not make any big difference.

FIG. 23 shows that the regularized mesh has large difference to the original mesh in the regions of high curvature. In the measurement above the difference on a molar is 336 microns, which is clearly not satisfactory for an accurate and high-quality simulation.

After calculating the 3d positions of the regularized mesh vertices one iterates through its facets, finds the closest point from its midpoint to the original mesh and if the difference is larger than a threshold T, one marks this facet for subdivision. In this way one can iteratively subdivide the facets of the regular base mesh until a desired precision is reached.

Figure 23B:
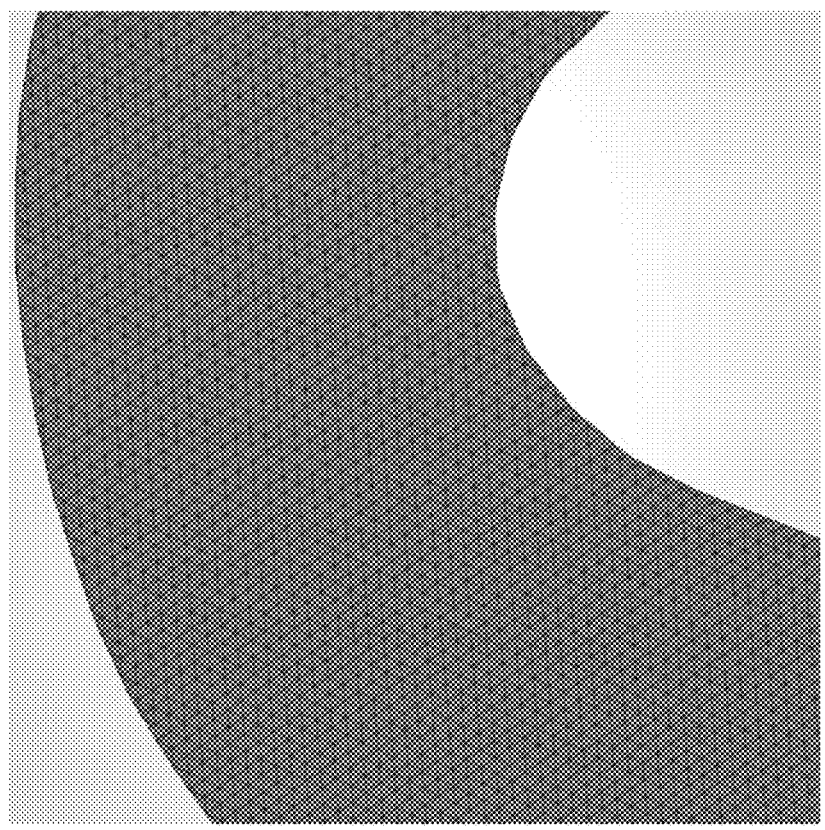
Figure 23A:
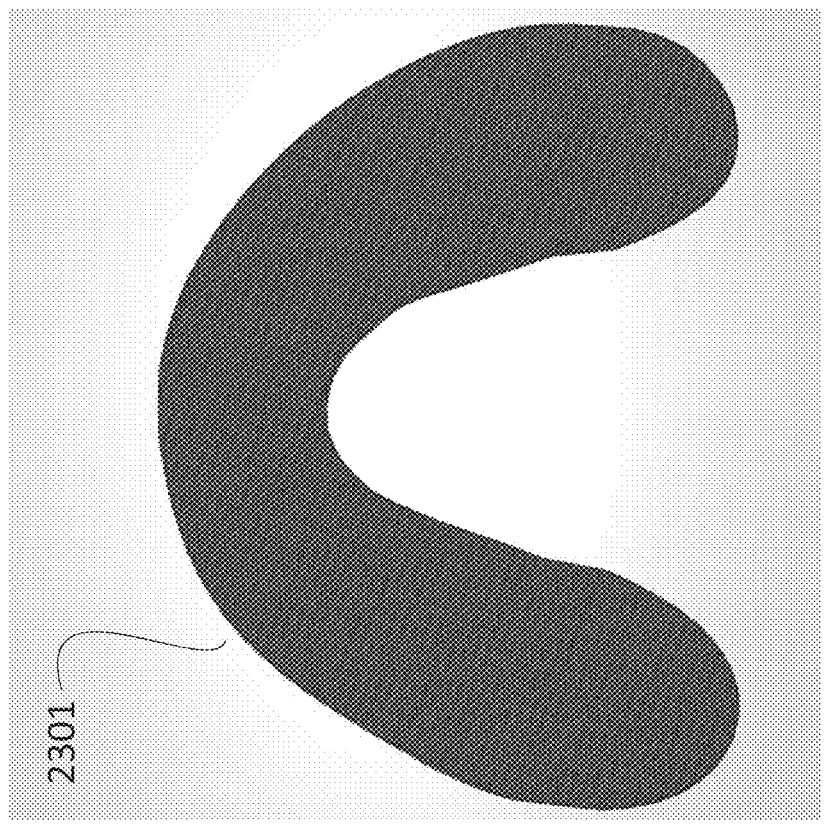
Figure 23D:
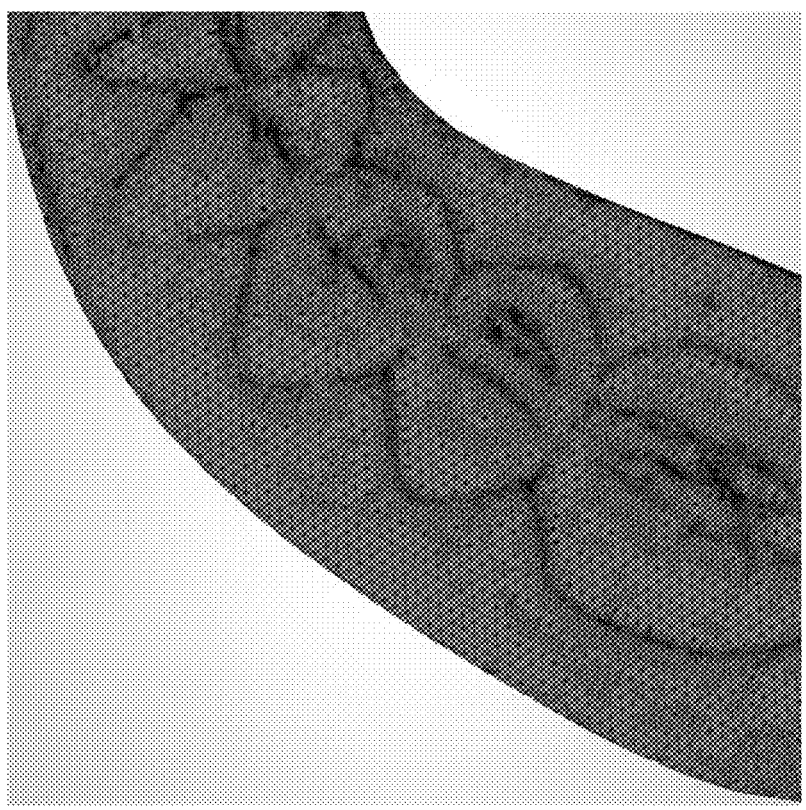
Figure 23C:
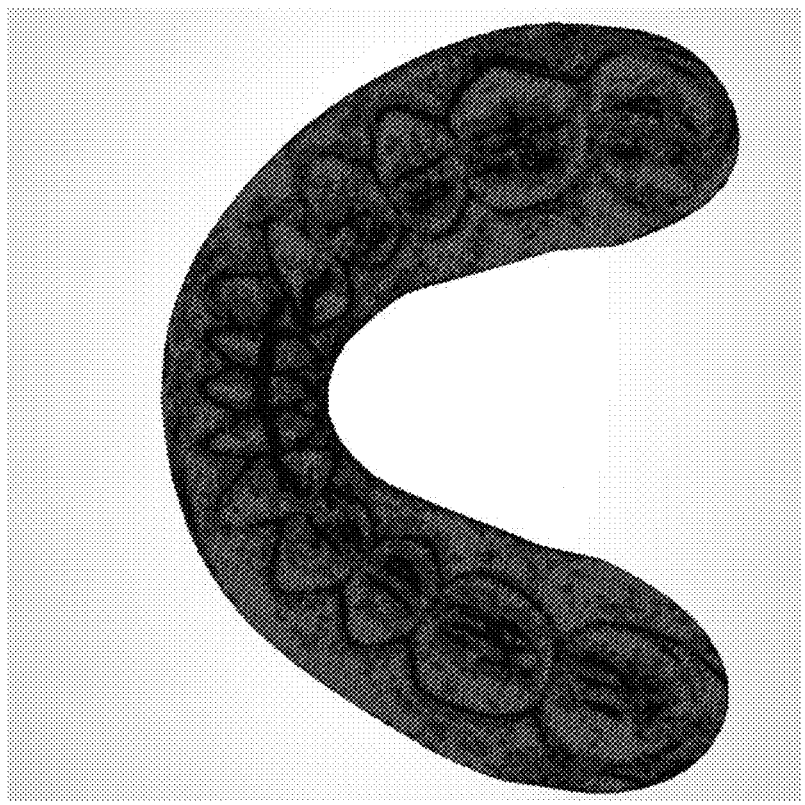

After the first adaptive refinement step, a considerable improvement is achieved because the high curvature areas have more facets, as seen in FIGS. 23c and 23d, and so the regular mesh is much better adapted to the geometry of the original mesh.

In the final step of the algorithm all the facets meet the minimal distance requirement to the original model.

Figure 24:
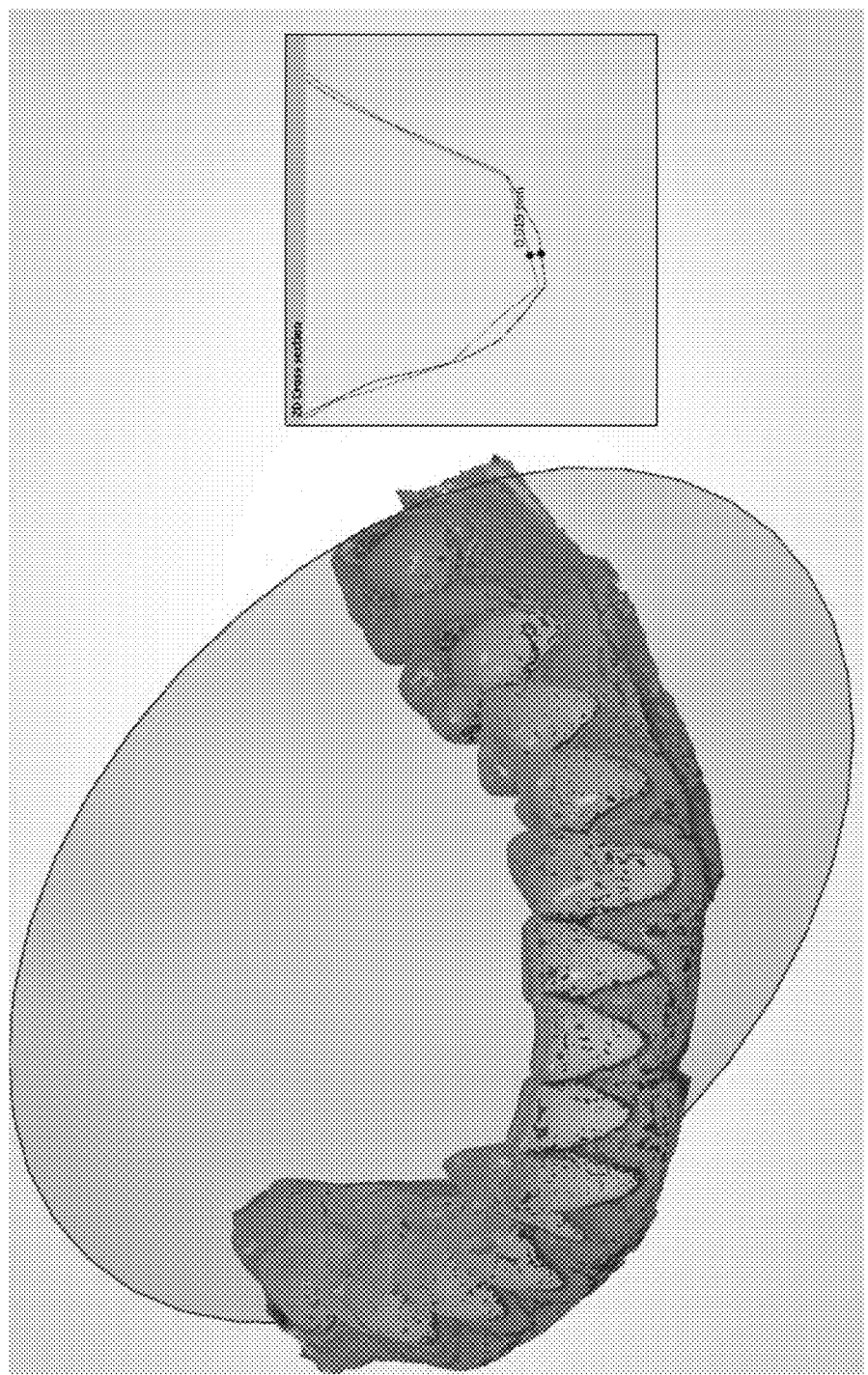

One can see from FIG. 24 that on every point the maximal distance is less than 20 microns.

Figure 25:
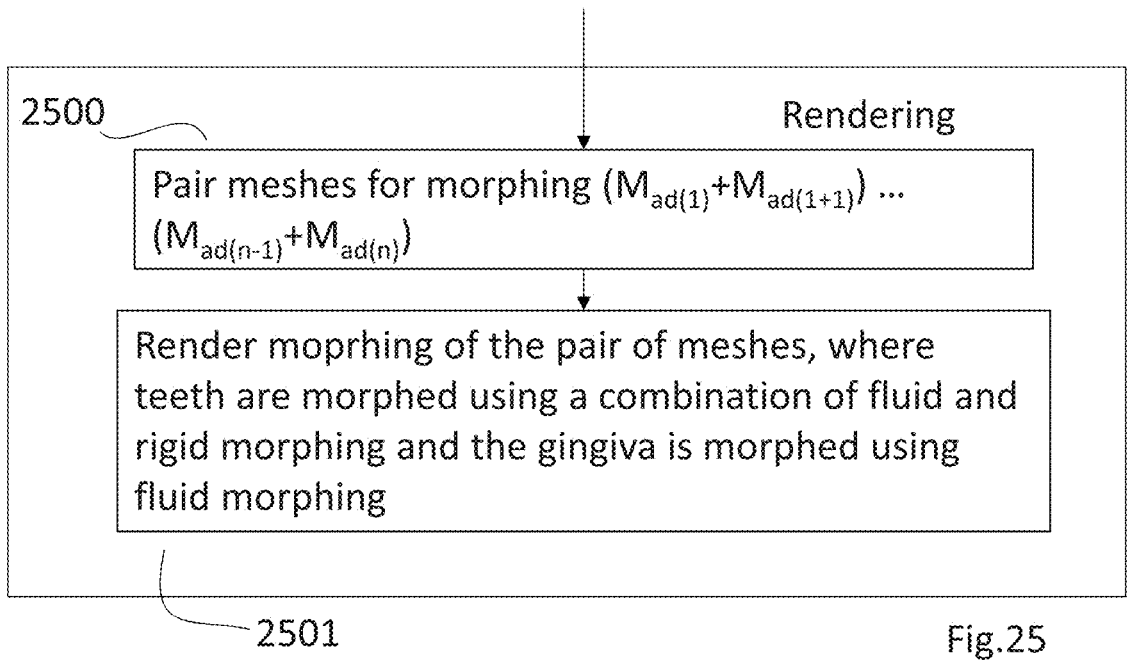

Finally the scans have been prepared for rendering as shown in the rendering process of FIG. 25.

After all the regular meshes for the input models have been generated, we group them into pairs, ($M_{ad(1)}$+$M_{ad(1+1)}$) . . . ($M_{ad(n-1)}$+$M_{ad(n)}$) in step 2500. We have extended the standard mesh data structure with additional data to be sent to the graphic card, in order to get a smooth morphing. We call this a morphable mesh. Given two segmented jaw scans with the same topology we save the vertex positions vi and the corresponding v'i, vertex normal ni and the corresponding n'i, texture coordinates uvi with correspondence uv'i, segment UNN number s=0, 1, . . . , 32 for each vertex indicating if it belongs to the gingiva or a tooth with given UNN, and for each UNN a matrix giving the rigid tooth to tooth transformation. For each pair this data is saved and sent to the shader for animating the morphing between models.

Step 2501 performs the actual rendering of the pairs.

Using pairs of consecutive regular meshes (Ri, Ri+1), we generate the interpolated vertex position post(v) for a value tin [0,1] in a specific way.

Based on the segmentation previously vertices relating to teeth and gingiva respectively have already been identified. Accordingly, specific teeth-to-teeth alignment matrices Ts (Ri, Ri+1)=Ts, can be used for each tooth segment with unn number s. The matrix T's that transforms the tooth segment from Ri+1 to Ri is given by the inverse matrix (Ts)−1 of Ts (Ri, Ri+1).

In the first step we interpolate two different matrices Ts (t) and Ts (t) and T's (1−t) for the partial alignments from Ri to Ri+1 in interval t and partial alignments from Ri+1 to Ri in interval 1−t. We then generate two intermediate point values:

alignmentPost($vi$)=(1−$t$)×$vi$+$t$×$Ts$($t$)($vi$)

alignmentPos1−$t$($vi$+1)=(1−$t$)×$T's$(1−$t$)($vi$+1)+$t$×$vi$+1

The final interpolation is given by $$\text{post}(v) = (1-t) \times \text{alignmentPost}(vi) + t \times \text{alignmentPost1} - t(vi+1) = (1-t)2 \times vi + t \times (1-t) \times [Ts(t) \times (vi) + T's(1-t) \times (vi+1)] + t \times vi + 1$$

In this way a morphing is rendered which is a balanced combination of smooth transition between two jaw models combined with rigid tooth movement. In particular it is possibly to apply different weights to how much rigid morphing is desired and how much should be fluid. Typically a high percentage, e.g. 70%, should be rigid since it can be expected that the teeth are the same from scan to scan. However, some morphing should be fluid since teeth can have been chipped or worn.

We use the same approach to calculate the intermediate values of the normal at each vertex. The texture is interpolated with a simple linear interpolation. The morphing data for all the pairs is pushed to the graphic card in one go. As the animation runs, we determine which pair of models is active in the animation and only render the scene for that corresponding pair.

Finally there may be some special cases that may need to be considered in order to give a user the best experience.

For example morphing a tooth to gingiva should be considered when a tooth has been removed between two scans, for example due to extraction of the tooth.

Also morphing between a partial and full scan or vice versa can be considered when some scans are not complete but contain relevant data for certain areas.

In the two above cases instead of morphing a transition using transparency is applied. The full tooth disappears, and the gingiva slowly appears on the scene. Likewise, the full model disappears using transparency and the overlapping part morphs into the partial model.

In addition there may be cases when one of the model has texture and the other has none. In such cases a predefined color is used to render the model without texture and morph its color into the texture.

In another aspect a user interface 2600 is shown in FIG. 26 for aiding a user for selecting a plurality of scans from scan resource such as a database, a library or another resource where a large number of scans are stored or retained.

The scan resource will typically contain patient specific scans, so that the user is selecting scans from the same patient. However, for some use it may be relevant to select scans across different patients or people, e.g. in order to compare dental situation across age groups.

For example, the user interface may be used to select a plurality of scans for use in the method for presenting a graphical representation as disclosed herein. However, the user interface may also be used in other dental related application where a plurality of scan needs to be selected.

The user interface comprises a first image area 2601 where four of the plurality of scans 2602, 2603, 2604, 2605 are graphically represented by a 2D image thumbnail. Other types of graphical thumbnails can also be used, for example a thumbnail 3D image. The graphical thumbnails are in the current embodiment presented horizontally, however, they may be presented in many different configurations, such as in a grid view or vertically.

The thumbnails are presented together with other icons and text indicating relevant information about the scan, e.g. text indicating date the scan was taken 26021, 26031, 26041, text indicating how long ago the scan was taken 26022, 26032, 26042, 26052, icon showing the type of scan 26023, icons showing additional information about the scan 26054.)

The icon showing the type of scans can for example indicate that it is a intra oral scan of both upper and lower jaw 26023, 26033, 26043 or a scan of only one of the jaws 26053. The icons showing additional information can for example indicate fluorescence data 26054 or color data 26055.

Since not all the scans from the scan resource can fit in the first image area arrows 2606, 2607 are provided for horizontal scrolling between the image representations.

In a second timeline area 2610 a time line 2611 is shown wherein markers 2612 are placed. The markers represent the different scans in the scan resource from which the plurality of scans is to be selected. In the current embodiment it can be seen that the first scan in the scan resource is from the year 2016 and the newest scan is from October, 2019.

In the current setup a user have selected two scans 2604, 2605 in the first image area 2601 have been selected. This is reflected in the timeline 2611 where two markers 26121 and 26122 have been highlighted to indicate this selection in the timeline.

Thus as can be understood the timeline gives a good overview of all the scans in the scan resource, while the first image area provides a more detailed view having the information necessary for the user to decide if a scan should be selected for further processing.

When the desired scans have been selected the user can send these plurality of scans for further processing, for example in the method for graphically presenting a plurality of scans as disclosed herein.

In order to further aid the user in choosing scans a third search area 2620 is provided where search filters 2621,2622 are provided. This allows the user to search for specific time periods, search for full jaw scans only, or color scans only.

A particular advantageous feature for grouping the scans is the timeline view 2622. In FIG. 22 this is set to timeline view which shows the scans taken sorted consecutively by time it was taken. However, an indication view can also be chosen and the scans will be sorted by which indication they were taken. E.g. if a clear aligner treatment has been performed on the user the clear aligner view can be selected and all the scans for such treatment is shown. Other treatments can for example be other orthodontic treatment, such as bracket treatment, or restorative treatment, e.g. a crown or bridge, implant treatment and many others. Such indication view is very advantageous to the user as it is often more interesting to monitor treatment progress for specific treatment/indication types instead of choosing arbitrary scans from a large pool of scans taken over a long time.

In addition to searching and filtering scans additional tags can be added. For example, the "Baseline" tag 2630 and the "New" tag 2631 has been added to scan 2602 and 2605 respectively. This allows the user to do quick selection by using one of the hotkeys in the fourth hotkey area 2640. Three hotkeys 2641, 2642, 2643 are shown in the current embodiment. The first hotkey 2641 selects all the scans at once. The second hotkey selects the two most recent scans for processing. The third hotkey takes the "Baseline" scan and the "New" scan and sends these on to further processing.

Furthermore, different types of custom user defined tags may be added to individual scans and subsequently used for filtering purposes. Such custom tags could be clinical observations or comments directly added to individual scan meta data. Intelligent search engines may group related tags and present a reduced list for the user when filtering. Such clinical comments could be: gingivitis progress, caries progress, tooth erosion progress.

In order to further process the selected plurality of scans the user will click the "Confirm and Continue" button 2650. Here it is also shown how many scans the user have selected out of the scan resource.

Figure 27:
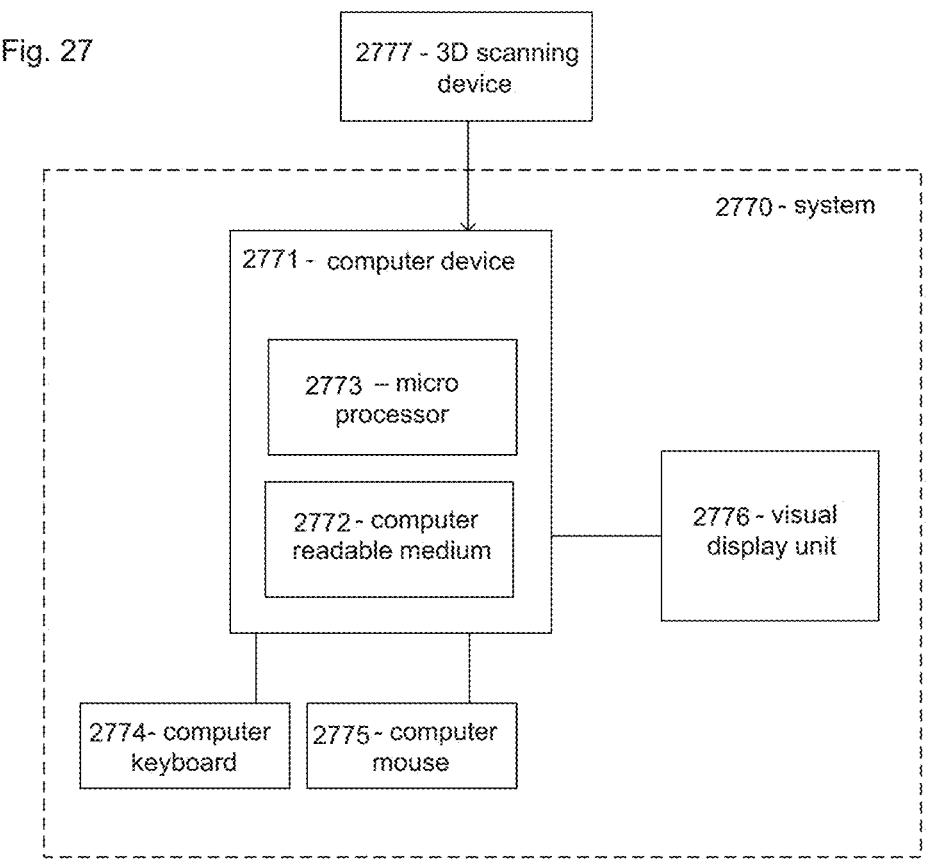

The method for presenting a graphical representation and a user interface for selecting a plurality of scans as disclosed herein can for example be implemented in a computer system 2770 commonly known in the art, as shown in FIG. 27.

The computer system comprises a computer device 2771, such as a standard laptop or desktop PC. The computer device comprises a computer readable medium 2772 for storing and reading data, for example program code or data representing the plurality of scans. The computer readable medium 2772 can for example be a hard drive or RAM. In order to execute the method disclosed a micro processor 2773 will read the program code and execute it.

A visual display unit 2776, such as a computer monitor or AR/VR googles, can be used to present the user interface for selecting a plurality of scans and/or subsequently present the graphical representation of the oral situation of the patient over time as disclosed herein based on the executed program code.

Input devices, such as a computer keyboard 2774 or computer mouse 2775, are provided to give input to the computer. The input can for example be to for a user to select and load the plurality of scans from a database. Alternatively, it can be to activate a 3D scanning device 2777 which is connected to the system in order to obtain a scan of the patient which can be used and compared with historical records comprising previous scans.

Accordingly, the step of obtaining a plurality of scans may for example provided by the micro processor 2773 retrieving the scans from a database. The step of determining at least one boundary may be provided by the micro processor by executing program code stored on the computer readable medium 2772. The step of presenting the plurality of scans can for example be done by the visual display unit 2776.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

The term "obtaining" as used in this specification may refer to physically acquiring for example medical images using a medical imaging device, but it may also refer for example to loading into a computer an image or a digital representation previously acquired.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

Embodiments

1. A computer implemented method for presenting a graphical representation of an oral situation of a patient over time, wherein the method comprises, obtaining a plurality of scans, each scan representing the oral situation of the patient at a specific time, and where each scan comprises a scan boundary defining the extent of the scan, determining at least one modified boundary, and presenting the plurality of scans in a time sequence wherein the scan boundary of each of the respective plurality of scans has been modified based on one of the at least one modified boundary.

2. A method according to embodiment 1, wherein the step of presenting the plurality of scans in a time sequence wherein the scan boundary of each of the respective plurality of scans has been modified based on one of the at least one modified boundary further comprises that the at least one modified boundary is used as a reference for morphing between at least two of the plurality of scans in a time sequence.

3. A method according to embodiment 2, wherein a base domain is defined based on the at least one modified boundary.

4. A method according to embodiment 3, wherein a regular mesh generated within the at least one modified boundary.

5. A method according to embodiment 4, wherein the regular mesh is refined by applying the plurality of scans to the mesh and remeshing by determining the closest point from the midpoint of a facet in the regular mesh to the respective facet in each of the plurality of scans and if the difference is larger than a threshold the facet is subdivided.

6. A method according to embodiment 5, wherein the refined regular mesh is applied to the plurality of scans.

7. A method according to any one of the embodiment 1-6, wherein at least some of the vertices of each scan and/or the applied refined regular mesh is assigned as representing either gingiva or a tooth of the patient.

8. A method according to embodiment 7, wherein the morphing between corresponding vertices of two scans of the plurality of scans is rendered according to a gingiva transformation if the corresponding vertices represent gingiva and a tooth transformation if the corresponding vertices represent a tooth, wherein the gingiva transformation and the tooth transformation are different.

9. A method according to embodiment 8, wherein the tooth transformation has a higher weight of rigid transformation than the gingiva transformation.

10. A method according to embodiment 9, wherein the gingiva transformation is a fluid transformation and wherein the tooth transformation a combined rigid and fluid transformation where at least 50% is a rigid transformation, preferably at least 60% in particular at least 70%.

11. A method according to embodiment 10, wherein the rigid transformation comprises preserving at one or more of the following mesh metrics, angle between edges, angle between faces and length between vertices.

12. A method according to embodiment 11, wherein the fluid transformation do not preserve at least one of the mesh metrics which the transformation preserve.

13. A method according to embodiment 3, fitting a plane through the at least one modified boundary, projecting the at least one modified boundary to the plane and defining the base domain as the plane defined by the projected at least one modified boundary.

14. A method according to any one of the embodiments 2-13, wherein the scan boundary of the plurality of scans is set as the at least one modified boundary.

15. A method according to any one of the embodiments 2-14, wherein each of the plurality of scans are mapped to the base domain.

16. A method according to embodiment 15, wherein each of the plurality of scans are flattened to the base domain.

17. A method according to embodiment 15 or 16, wherein a predetermined mesh is applied to each of the plurality of scans when mapped to the base domain.

18. A method according to embodiment 17, wherein the plurality of scans are returned to the 3D domain.

19. A method according to embodiment 18, wherein the plurality of scans are returned to the 3D domain by returning the vertices of the predetermined mesh into the 3D domain.

20. A method according to embodiment 19, wherein morphing between the plurality of scans in a time sequence is provided by linearly transforming between corresponding vertices in the predetermined mesh of the respective plurality of scans.

21. A method according to embodiment 1, wherein the step of presenting the plurality of scans in a time sequence wherein the scan boundary of each of the respective plurality of scans has been modified based on one of the at least one modified boundary, comprises that the scan boundary of each of the respective plurality of scans is at least partly modified to one of the at least one modified boundary.

22. A method according to embodiment 21, wherein the at least one modified boundary is a pre-set boundary.

23. A method according to embodiment 21 or 22, wherein the at least one modified boundary is determined based on a reference scan selected from the plurality of scans.

24. A method according to embodiment 21, 22 or 23, wherein the scan boundary of the reference scan is set as the at least one modified boundary.

25. A method according to embodiment 21, 22, 23 or 24, wherein the at least one modified boundary is determined based on at least two of the plurality of scans.

26. A method according to embodiment 25, wherein the determining the at least one modified boundary based on at least two of the plurality of scans comprises, determining at least a first and a second scan boundary of the at least two of the plurality of scans respectively, and determining the at least one modified boundary based on an average boundary of the at least first and second scan boundary.

27. A method according to embodiment 26, wherein determining the at least one modified boundary further comprises the step of smoothing the average boundary.

28. A method according to embodiment 26 or 27, wherein each of the at least first and second boundary are smoothed before determining the at least one modified boundary.

29. A method according to any one of the embodiments 1-19, wherein a plurality of modified boundaries are determined comprising at least a first and a second modified boundary.

30. A method according to embodiment 29, wherein the first common and second modified boundary are pre-set boundaries with a different size and/or shape.

31. A method according to embodiment 29, wherein the first modified boundary is determined based on at least two of the plurality of scans and wherein the second modified boundary is determined based on at least two of the plurality of scans, where at least one of the two of the plurality of scans for determining the second modified boundary is different from the at least two of the plurality of scans for determining the first modified boundary.
32. A method according to embodiment 29, 30 or 31, wherein the first modified boundary is a pre-set boundary and the second modified boundary is determined based on at least two of the plurality of scans.
33. A method according to embodiment 29, 30, 31 or 32, wherein the scan boundaries of the scans of a first group of the plurality of scans is modified to the first modified boundary, and the scan boundaries of the scans of a second group comprising scans different from the first group of the plurality of scans is modified to the second modified boundary.
34. A method according to embodiment 29, 30, 31, 32 or 33, wherein the plurality of modified boundaries further comprises a third or more modified boundaries comprising either a pre-set boundary or a boundary determined based on at least two of the plurality of scans.
35. A method according to embodiment 33 and 34, comprising a third or more group comprising a number of the plurality of scans different from the scans of the other groups, where the scan boundaries of the scans of the third group or more groups are modified to the third or more modified scan boundaries respectively.
36. A method according to embodiment 33 or 35, wherein the first, second, third and/or more groups are determined based on one or more time variable of the scans in the respective groups.
37. A method according to embodiment 36, wherein the time variable is the age of the patient when the specific scan was taken.
38. A method according to embodiment 36 or 37, wherein the time variable is a patient size parameter taken when the specific scan was taken, such as height and/or weight.
39. A method according to embodiment 36, 37 or 38, wherein the time variable is the time from when a dental treatment was initiated or completed.
40. A method according to any one of the embodiments 33-39, wherein the first, second, third and/or more groups are determined based on one or more patient characteristic, such as sex.
41. A method according to any one of the embodiments 1-40, wherein the scan boundary of at least two scans are modified to have the same at least one modified boundary.
42. A method according to any one of embodiments 1-41, wherein the at least one modified boundary is set to be the scan boundary of one of the plurality of scans and wherein the scan boundary of at least a second of the plurality of scans is modified to the at least one modified boundary.
43. A method according to any one of the embodiments 1-42, wherein the at least one modified boundary is a closed spline.
44. A method according to embodiment 43, wherein the closed spline is used a cutting spline for removing scan data outside the cutting spline.
45. A method according to embodiment 43 or 44, wherein the closed spline is used as a fill spline for adding data to the scan data within the fill spline.
46. A method according to any one of the embodiments 1-45, where the plurality of scans are obtained as voxel data.
47. A method according to any one of the embodiments 1-46, where the plurality of scans are treated/obtained as surface data.
48. A method according to embodiment 47, wherein the surface data has been further processed so that the plurality of scans are obtained/treated as volumetric data.
49. A method according to any one of the embodiments 1-48, wherein at least one of the plurality of scans is further processed between obtaining the scans and presenting the plurality of scans.
50. A method according to any one of the embodiments 1-49, wherein the plurality of scans are segmented to digitally identify teeth of the scans and gingiva of the scans.
51. A user interface for facilitating the selection of a plurality of scans from a scan resource comprising scans taken over time, wherein the user interface comprises a first image area wherein at least an image thumbnail of at least a number of scans are shown, and a second timeline area wherein a visual marker is provided for at least the number of scans in the first image area, and wherein the user interface comprises a highlight of a visual marker in the time line if the corresponding thumbnail image is selected by user interaction in the first image area.
52. A user interface for facilitating the selection of a plurality of scans from a scan resource comprising scans taken over time, wherein the user interface comprises a first image area wherein at least an image thumbnail of at least a number of scans are shown, and a second timeline area wherein a visual marker is provided for at least the number of scans in the first image area, and wherein the user interface comprises a highlight of a thumbnail image in the first image area if the corresponding visual marker is selected by user interaction in the time line.
53. A user interface according to embodiment 51 or 52, wherein a visual marker is provided on the time line for each of the scans in the scan resource.
54. A user interface according to embodiment 51, 52 or 53, wherein the scans are sorted by indication.
55. A user interface according to any one of the embodiment 51-54, wherein the thumbnail in the first image area represent a subset of the scans from the scan resource.
56. A user interface according to claim 55, wherein the subset is selected based on a filtering requirement determined by the user through user interaction.
57. A user interface according to claim 56, wherein the filtering requirement for example can be selected from a group comprising one or more, indications (ortho treatment, brackets, clear aligner, restorative treatment, crowns, bridges, implants, drill guides, dentures), tooth wear, color scans, fluorescence scans, full arch scans, caries, surgery.
58. A user interface according to any one of the embodiments 51-57, comprises a user interaction where the user can forward the selected scan as a plurality of scans for further processing, e.g. in a computer implemented method according to embodiments 1-50.

The invention claimed is:

1. A computer implemented method for presenting a graphical representation of an oral situation of a patient over time, wherein the method comprises,
    obtaining a plurality of scans, each scan representing the oral situation of the patient at a specific time, and where each scan comprises a scan boundary defining the extent of the scan,
    determining at least one modified boundary, and
    presenting the plurality of scans in a time sequence wherein the scan boundary of each of the respective plurality of scans has been modified based on one of the at least one modified boundary.

2. A method according to claim 1, wherein the step of presenting the plurality of scans in a time sequence wherein the scan boundary of each of the respective plurality of scans has been modified based on one of the at least one modified boundary further comprises that the at least one modified boundary is used as a reference for morphing between at least two of the plurality of scans in a time sequence.

3. A method according to claim 2, wherein a base domain is defined based on the at least one modified boundary.

4. A method according to claim 1, wherein the step of presenting the plurality of scans in a time sequence wherein the scan boundary of each of the respective plurality of scans has been modified based on one of the at least one modified boundary, comprises that the scan boundary of each of the respective plurality of scans is at least partly modified to one of the at least one modified boundary.

5. A method according to claim 4, wherein the at least one modified boundary is a pre-set boundary.

6. A method according to claim 4, wherein the at least one modified boundary is determined based on a reference scan selected from the plurality of scans.

7. A method according to claim 6, wherein the scan boundary of the reference scan is set as the at least one modified boundary.

8. A method according to claim 4, wherein the at least one modified boundary is determined based on at least two of the plurality of scans.

9. A method according to claim 8, wherein the determining the at least one modified boundary based on at least two of the plurality of scans comprises,
    determining at least a first and a second scan boundary of the at least two of the plurality of scans respectively, and
    determining the at least one modified boundary based on an average boundary of the at least first and second scan boundary.

10. A method according to claim 1, wherein a plurality of modified boundaries are determined comprising at least a first and a second modified boundary.

11. A method according to claim 10, wherein a first common and second modified boundary are pre-set boundaries with a different size and/or shape.

12. A method according to claim 10, wherein the first modified boundary is determined based on at least two of the plurality of scans and wherein the second modified boundary is determined based on at least two of the plurality of scans, where at least one of the two of the plurality of scans for determining the second modified boundary is different from the at least two of the plurality of scans for determining the first modified boundary.

13. A method according to claim 10, wherein the scan boundaries of the scans of a first group of the plurality of scans is modified to the first modified boundary, and the scan boundaries of the scans of a second group comprising scans different from the first group of the plurality of scans is modified to the second modified boundary.

14. A method according to claim 13, wherein the first and second and/or more groups are determined based on one or more time variable of the scans in the respective groups.

15. A method according to claim 10, wherein the plurality of modified boundaries further comprises a third or more modified boundaries comprising either a pre-set boundary or a boundary determined based on at least two of the plurality of scans.

16. A method according to claim 1, wherein the scan boundary of at least two scans are modified to have the same at least one modified boundary.

* * * * *